US009149836B2

(12) United States Patent
Whiteford et al.

(10) Patent No.: US 9,149,836 B2
(45) Date of Patent: Oct. 6, 2015

(54) COMPOSITIONS AND METHODS FOR MODULATION OF NANOSTRUCTURE ENERGY LEVELS

(71) Applicant: SanDisk Corporation, Milpitas, CA (US)

(72) Inventors: Jeffery A. Whiteford, Belmont, CA (US); Mihai A. Buretea, San Francisco, CA (US); Jian Chen, Mountain View, CA (US); William P. Freeman, San Mateo, CA (US); Andreas Meisel, San Francisco, CA (US); Linh Nguyen, San Jose, CA (US); J. Wallace Parce, Palo Alto, CA (US); Erik C. Scher, San Francisco, CA (US)

(73) Assignee: SanDisk Corporation, Milpitas, CA (US)

( * ) Notice: Subject to any disclaimer, the term of this patent is extended or adjusted under 35 U.S.C. 154(b) by 0 days.

(21) Appl. No.: 14/018,260

(22) Filed: Sep. 4, 2013

(65) Prior Publication Data

US 2014/0017396 A1     Jan. 16, 2014

Related U.S. Application Data

(60) Division of application No. 11/299,299, filed on Dec. 9, 2005, now Pat. No. 8,563,133, which is a continuation-in-part of application No. 11/147,670, filed on Jun. 7, 2005, now Pat. No. 7,267,875.

(60) Provisional application No. 60/635,799, filed on Dec. 13, 2004, provisional application No. 60/578,236, filed on Jun. 8, 2004, provisional application No. 60/632,570, filed on Nov. 30, 2004.

(51) Int. Cl.
*B05D 5/12*    (2006.01)
*C07F 5/02*    (2006.01)

(52) U.S. Cl.
CPC . *B05D 5/12* (2013.01); *C07F 5/025* (2013.01); *Y10T 428/2982* (2015.01); *Y10T 428/2991* (2015.01); *Y10T 428/2993* (2015.01); *Y10T 428/2995* (2015.01); *Y10T 428/2996* (2015.01); *Y10T 428/2998* (2015.01)

(58) Field of Classification Search
CPC ..... B05D 5/12; C07F 5/025; Y10T 428/2996; Y10T 428/2991; Y10T 428/2995; Y10T 428/2998; Y10T 428/2993; Y10T 428/2982
USPC .................... 427/77; 428/403, 404
IPC ................. H01L 2924/0002, 2924/00
See application file for complete search history.

(56) References Cited

U.S. PATENT DOCUMENTS

| | | |
|---|---|---|
| 3,514,320 A | 5/1970 | Vaughan |
| 5,043,940 A | 8/1991 | Harari |
| 5,434,825 A | 7/1995 | Harari |
| 5,505,928 A | 4/1996 | Alivisatos et al. |
| 5,609,907 A | 3/1997 | Natan |
| 5,690,807 A | 11/1997 | Clark, Jr. et al. |
| 5,701,221 A | 12/1997 | Taniyama et al. |
| 5,751,018 A | 5/1998 | Alivisatos et al. |
| 5,897,945 A | 4/1999 | Lieber et al. |
| 5,937,295 A | 8/1999 | Chen et al. |
| 5,938,934 A | 8/1999 | Balogh et al. |
| 5,990,479 A | 11/1999 | Weiss et al. |
| 5,997,832 A | 12/1999 | Lieber et al. |
| 6,036,774 A | 3/2000 | Lieber et al. |
| 6,048,616 A | 4/2000 | Gallagher et al. |
| 6,054,349 A | 4/2000 | Nakajima et al. |
| 6,090,666 A | 7/2000 | Ueda et al. |
| 6,107,008 A | 8/2000 | Howell et al. |
| 6,136,156 A | 10/2000 | El-Shall et al. |
| 6,139,626 A | 10/2000 | Norris et al. |
| 6,159,620 A | 12/2000 | Heath et al. |

(Continued)

FOREIGN PATENT DOCUMENTS

| | | |
|---|---|---|
| CN | 1195861 A | 10/1998 |
| CN | 1320931 A | 4/2001 |
| EP | 1034234 | 7/2003 |
| EP | 1034234 B1 | 7/2003 |
| EP | 1386362 B1 | 1/2007 |
| JP | 2000-022129 A | 1/2000 |
| JP | 2001-520937 | 11/2001 |
| JP | 2004515782 A | 5/2004 |
| WO | 99/01766 | 1/1999 |
| WO | 99/21934 | 5/1999 |

(Continued)

OTHER PUBLICATIONS

Third Office Action in related Chinese Application No. 201010503565.3 dated Jun. 3, 2013.

(Continued)

*Primary Examiner* — Leszek Kiliman
(74) *Attorney, Agent, or Firm* — Vierra Magen Marcus LLP

(57) ABSTRACT

Ligand compositions for use in preparing discrete coated nanostructures are provided, as well as the coated nanostructures themselves and devices incorporating same. Methods for post-deposition shell formation on a nanostructure, for reversibly modifying nanostructures, and for manipulating the electronic properties of nanostructures are also provided. The ligands and coated nanostructures of the present invention are particularly useful for close packed nanostructure compositions, which can have improved quantum confinement and/or reduced cross-talk between nanostructures. Ligands of the present invention are also useful for manipulating the electronic properties of nanostructure compositions (e.g., by modulating energy levels, creating internal bias fields, reducing charge transfer or leakage, etc.).

36 Claims, 10 Drawing Sheets

(56) References Cited

U.S. PATENT DOCUMENTS

| | | | |
|---|---|---|---|
| 6,207,229 B1 | 3/2001 | Bawendi et al. | |
| 6,222,762 B1 | 4/2001 | Guterman et al. | |
| 6,225,198 B1 | 5/2001 | Alivisatos et al. | |
| 6,275,419 B1 | 8/2001 | Guterman et al. | |
| 6,297,095 B1 | 10/2001 | Muralidhar et al. | |
| 6,306,736 B1 | 10/2001 | Alivisatos et al. | |
| 6,317,363 B1 | 11/2001 | Guterman et al. | |
| 6,317,364 B1 | 11/2001 | Guterman et al. | |
| 6,320,784 B1 | 11/2001 | Muralidhar et al. | |
| 6,322,901 B1 | 11/2001 | Bawendi et al. | |
| 6,340,822 B1 | 1/2002 | Brown et al. | |
| 6,344,403 B1 | 2/2002 | Madhukar et al. | |
| 6,413,489 B1 | 7/2002 | Ying et al. | |
| 6,413,819 B1 | 7/2002 | Zafar et al. | |
| 6,548,168 B1 * | 4/2003 | Mulvaney et al. | 428/402 |
| 6,563,260 B1 | 5/2003 | Yamamoto et al. | |
| 6,576,291 B2 | 6/2003 | Bawendi et al. | |
| 6,577,532 B1 | 6/2003 | Chevallier | |
| 6,586,785 B2 | 7/2003 | Flagan et al. | |
| 6,597,496 B1 | 7/2003 | Nayfeh et al. | |
| 6,614,069 B2 | 9/2003 | Rosner et al. | |
| 6,680,505 B2 | 1/2004 | Ohba et al. | |
| 6,723,606 B2 | 4/2004 | Flagan et al. | |
| 6,740,910 B2 | 5/2004 | Roesner et al. | |
| 6,784,103 B1 | 8/2004 | Rao et al. | |
| 6,872,645 B2 | 3/2005 | Duan et al. | |
| 6,878,871 B2 | 4/2005 | Scher et al. | |
| 6,891,319 B2 | 5/2005 | Dean et al. | |
| 6,927,454 B2 | 8/2005 | Chan et al. | |
| 6,936,484 B2 | 8/2005 | Kanechika et al. | |
| 6,949,206 B2 | 9/2005 | Whiteford et al. | |
| 6,984,842 B1 | 1/2006 | Nayfeh et al. | |
| 7,005,697 B2 | 2/2006 | Batra et al. | |
| 7,045,851 B2 | 5/2006 | Black et al. | |
| 7,067,867 B2 | 6/2006 | Duan et al. | |
| 7,070,472 B2 | 7/2006 | Dean et al. | |
| 7,186,381 B2 | 3/2007 | Penner et al. | |
| 7,199,393 B2 | 4/2007 | Park et al. | |
| 7,267,875 B2 * | 9/2007 | Whiteford et al. | 428/402 |
| 7,274,035 B2 | 9/2007 | Yang et al. | |
| 7,402,829 B2 | 7/2008 | Green | |
| 7,422,790 B1 | 9/2008 | Scher et al. | |
| 7,501,315 B2 | 3/2009 | Heald et al. | |
| 7,557,028 B1 | 7/2009 | Scher et al. | |
| 7,572,393 B2 | 8/2009 | Whiteford et al. | |
| 7,585,564 B2 | 9/2009 | Whiteford | |
| 7,692,218 B2 | 4/2010 | Barron et al. | |
| 7,723,186 B2 | 5/2010 | Purayath et al. | |
| 7,851,784 B2 | 12/2010 | Kastalsky | |
| 8,088,483 B1 | 1/2012 | Whiteford et al. | |
| 8,563,133 B2 * | 10/2013 | Whiteford et al. | 428/402 |
| 2001/0001703 A1 | 5/2001 | Takahashi et al. | |
| 2002/0066401 A1 | 6/2002 | Peng et al. | |
| 2002/0071952 A1 | 6/2002 | Bawendi et al. | |
| 2002/0117659 A1 | 8/2002 | Lieber et al. | |
| 2002/0118369 A1 | 8/2002 | Misewich et al. | |
| 2002/0137235 A1 | 9/2002 | Rohlfing | |
| 2002/0140023 A1 | 10/2002 | Ohba et al. | |
| 2002/0171125 A1 | 11/2002 | Bao et al. | |
| 2003/0039744 A1 | 2/2003 | Fan et al. | |
| 2003/0173541 A1 | 9/2003 | Peng et al. | |
| 2003/0194630 A1 | 10/2003 | Beck et al. | |
| 2003/0224286 A1 | 12/2003 | Barclay et al. | |
| 2003/0235064 A1 | 12/2003 | Batra et al. | |
| 2004/0000427 A1 | 1/2004 | Wang et al. | |
| 2004/0023010 A1 | 2/2004 | Bulovic et al. | |
| 2004/0026684 A1 | 2/2004 | Empedocles | |
| 2004/0038440 A1 | 2/2004 | Hatori | |
| 2004/0102050 A1 | 5/2004 | Delamarche et al. | |
| 2004/0191669 A1 | 9/2004 | Whitlock et al. | |
| 2004/0194295 A1 | 10/2004 | Green | |
| 2004/0228967 A1 | 11/2004 | Leung et al. | |
| 2004/0256667 A1 | 12/2004 | Oikawa et al. | |
| 2005/0072989 A1 | 4/2005 | Bawendi et al. | |
| 2005/0101063 A1 | 5/2005 | Tour et al. | |
| 2005/0122775 A1 | 6/2005 | Koyanagi et al. | |
| 2005/0139867 A1 | 6/2005 | Saito et al. | |
| 2005/0161666 A1 | 7/2005 | Park et al. | |
| 2005/0201149 A1 | 9/2005 | Duan et al. | |
| 2005/0202615 A1 | 9/2005 | Duan et al. | |
| 2005/0287717 A1 | 12/2005 | Heald | |
| 2006/0148177 A1 | 7/2006 | Kim | |
| 2006/0163646 A1 | 7/2006 | Black et al. | |
| 2007/0032091 A1 | 2/2007 | Heald et al. | |
| 2007/0293031 A1 | 12/2007 | Chan et al. | |
| 2008/0118755 A1 | 5/2008 | Whiteford et al. | |
| 2009/0155967 A1 | 6/2009 | Purayath et al. | |
| 2009/0170725 A1 | 7/2009 | Yamakawa et al. | |
| 2010/0155786 A1 | 6/2010 | Heald et al. | |

FOREIGN PATENT DOCUMENTS

| | | |
|---|---|---|
| WO | 0103208 | 1/2001 |
| WO | 0203430 A2 | 1/2002 |
| WO | 0217362 | 2/2002 |
| WO | 0248701 | 6/2002 |
| WO | 02/100867 | 12/2002 |
| WO | 2004/022714 | 3/2004 |
| WO | 2005001573 A2 | 1/2005 |
| WO | 2005017962 | 2/2005 |
| WO | 2005022120 | 3/2005 |
| WO | 2005023923 | 3/2005 |
| WO | 2006023037 A2 | 3/2006 |

OTHER PUBLICATIONS

Search Report in related Chinese Application No. 201010503565.3 dated May 28, 2013.

Jan. 11, 2013 Reply to Jul. 9, 2012 Office Action & Search Report of related Taiwan Patent Application No. 94117823. English translation only.

Office Action in related Korean Application No. 10-2007-7000514 dated Jan. 31, 2013.

Preliminary Amendment of related U.S. Appl. No. 11/147,670, filed Sep. 15, 2005.

Office Action of related U.S. Appl. No. 11/147,670 mailed Apr. 14, 2006.

May 22, 2006 Reply to Office Action of related U.S. Appl. No. 11/147,670.

Notice of Allowance and Examiner Interview Summary of related U.S. Appl. No. 11/147,670 mailed Jan. 4, 2007.

Preliminary Amendment of related U.S. Appl. No. 11/706,730, filed Feb. 13, 2007.

Preliminary Amendment of related U.S. Appl. No. 11/706,730, filed Mar. 29, 2007.

Preliminary Amendment of related U.S. Appl. No. 11/706,730, filed Apr. 19, 2007.

Office Action of related U.S. Appl. No. 11/706,730 mailed Jan. 9, 2008.

Supplemental Office Action of related U.S. Appl. No. 11/706,730 mailed Apr. 9, 2008.

May 7, 2008 Reply to Supplemental Office Action of related U.S. Appl. No. 11/706,730.

Office Action of related U.S. Appl. No. 11/706,730 mailed Aug. 20, 2008.

Nov. 3, 2008 Reply to Office Action of related U.S. Appl. No. 11/706,730.

Notice of Allowance of related U.S. Appl. No. 11/706,730 mailed May 8, 2009.

International Search Report & Written Opinion of International Patent Application No. PCT/US05/020100 dated Feb. 12, 2008.

Office Action & Search Report of related Taiwan Patent Application No. 94117823 dated Jul. 9, 2012.

Office Action & Search Report of related Malaysian Patent Application No. I20052518 dated Oct. 30, 2009.

Office Action of related Korean Patent Application No. 10-2007-7000514 dated Apr. 23, 2012.

Aug. 23, 2012 Reply to Apr. 23, 2012 Office Action of related Korean Patent Application No. 10-2007-7000514.

(56) References Cited

OTHER PUBLICATIONS

Office Action of related Japanese Patent Application No. 2007-527681 dated Aug. 29, 2011.
Dec. 16, 2011 Reply to Aug. 29, 2011 Office Action of related Japanese Patent Application No. 2007-527681.
Office Action of related Japanese Patent Application No. 2007-527681 dated Jun. 19, 2012.
Sep. 18, 2012 Reply to Jun. 19, 2012 Office Action of related Japanese Patent Application No. 2007-527681.
Office Action of related Chinese Patent Application No. 201010503565.3 dated Oct. 26, 2011.
Mar. 2, 2012 Reply to Oct. 26, 2011 Office Action of related Chinese Patent Application No. 201010503565.3.
Office Action of related Chinese Patent Application No. 200580018708.9 dated May 21, 2010.
Sep. 30, 2010 Reply to May 21, 2010 Office Action of related Chinese Patent Application No. 200580018708.9.
Office Action of related Chinese Patent Application No. 200580018708.9 dated Oct. 18, 2011.
Office Action of related Canadian Patent Application No. 2,567,907 dated Feb. 28, 2012.
Office Action of related Australian Patent Application No. 2005254490 dated Aug. 13, 2010.
Dec. 6, 2010 Reply to Aug. 13, 2010 Office Action of related Australian Patent Application No. 2005254490.
Office Action of related Australian Patent Application No. 2005254490 dated Jan. 7, 2011.
Feb. 17, 2011 Reply to Jan. 7, 2011 Office Action of related Australian Patent Application No. 2005254490.
Second Office Action in related Chinese Application No. 201010503565.3 dated Oct. 10, 2012.
Dec. 25, 2012 Response to Oct. 10, 2012 Second Office Action in related Chinese Application No. 201010503565.3.
Dec. 14, 2011 Reply to Oct. 18, 2011 Office Action of related Chinese Patent Application No. 200580018708.9.
Cassagrleau, T. et al., "Contiguous Silver Nanoparticle Coatings on Dielectric Spheres," Advanced Materials (2002) 14(10):732-736.
Sunahara, K. et al., "New BST-silica suspension coating material for dielectric thin films fabricated at low temperatures" Adv Appl Ceramics (2006) 105(3):153-157.
Fan et al. "Three-Dimensionally Ordered Gold Nanocrystal/Silica Superlattice Thin Films Synthesized via Sol-Gel Self Assembly" Adv. Func. Mat. (2006) 16:891-895.
Lim, et al. "Nonvolatile MOSFET memory based on high density WN nanocrystal layer fabricated by novel PNL (Pulse Nucleation Layer) method" Symp on VLSI Tech Digest of Tech Papers (2005) pp. 190-191.
Fan et al., (2000) "Rapid prototyping of patterned functional nanostructures," Nature, 405:56-60.
Gerion et al. (2001) "Synthesis and properties of biocompatible water-soluble silica-coated CdSe/ZnS semiconductor quantum dots," J. Phys. Chem. B, 105:8861-8871.
Giersig et al., (1997) "Direct observations of chemical reactions in silica-coated gold and silver nanoparticles", Adv. Mater., 9(7):570-575.
Schroedter & Weller (2002) "Ligand design and bioconjugation of colloidal gold nanoparticles" Angew. Chem., 41 (17):3218-3221.
Bruchez et al., (1998) "Semiconductor nanocrystals as fluorescent biological labels" Science 281:2013-2016.
Correa-Duarte et al. (1998) "Stabilization of CdS semiconductor nanoparticles against photodegradation by a silica coating procedure" Chemical Physics Letters 286:497-501.
Liz-Marzan et al. (1996) "Synthesis of nanosized-gold-silica core-shell particles," Langmuir, 12:4329-4335.
Schmid, G. et al., "Silsesquioxanes as ligands for gold clusters" Eur. J. Inorg. Chem. (1998) 813-817.
Schubert, U. "Polymers Reinforced by Covalently Bonded Inorganic Clusters" Chem. Mater. (2001) 13:3487-3494.
Sellier, C. et al. "Crystal structure and charge order below the metal-insulator transition in the vanadium bronze β-SrV6O15" Solid State Sciences (2003) 5:591-599.
Suzuki, A. "Recent Advanced in the Cross-Coupling Reactions of Organoboron Derivatives with Organic Electrophiles 1995-1998" J. Organomet. Chem. (1999) 576:147-168.
Takata, M. et al. "Fundamental characteristics of new non-volatile memory with extremely high density metal quantum dots" (Publication and publication Date unknown).
Tiwari, S. et al., "Volatile and Non-Volatile Memories in Silicon with Nano-Crystal Storage," IEDM (1995) 95:521-527.
Tiwari, S. et al., "A silicon nanocrystals based memory" Appl. Phys. Lett (1996) 68(10:1377-1379).
Urban, J.J. et al. "Synthesis of single-crystalline perovskite nanowires composed of barium titanate and strontium titanate" J. Am. Chem. Soc. (2002) 124:1186-1187.
Vampola, K. et al., "Growth and Characterization of metal nanocrystals" Cornell Nanofabrication Facility (Publication date unknown).
Weinstock, I.A. "Homogeneous-Phase Electron-Transfer Reactions of Polyoxometalates" Chem. Rev. (1998) 98:113-170.
Wu, Y. et al. "Block-by-block growth of single-crystalline Si/SiGe superlattice nanowires" Nano Letters (2002) 2:83-86.
Yamase, T. "Photo- and electrochromism of polyoxometalates and related materials" Chem. Rev. (1998) 98:307-325.
Yang, C-C. et al. "Characterization of poly(silsesquioxane) by thermal curing" Proc. Natl. Sci. Counc. ROC (2001) 25:339-343.
Yun, W.S. et al. "Ferroelectric Properties of Individual Barium Titanate Nanowires Investigated by Scanned Probe Microscopy" Nanoletters (2002) 2:447-450.
Zhang, K-Q. et al. "In situ observation of colloidal monolayer nucleation driven by an alternating electric field" Nature (2004) 429:739-743.
ISSCC delegates eye successor to floating gate flash memory http://www.electronicsweekly.com/article4907.htm Feb. 25, 2004.
Silicon Storage Technology, Inc. "Technical Comparison of Floating Gate Reprogrammable Nonvolatile Memories" Technical Paper, Nov. 2001 (Copyright 2002), 8 pages.
Rosario et al. (2004) "Lotus effect amplifies light-induced contact angle switching" Journal of Physical Chemistry: B 108:12640-12642.
Response to Restriction Requirement filed Feb. 18, 2010 in U.S. Appl. No. 11/299,299.
Requirement for Restriction/Election mailed Feb. 3, 2010 in U.S. Appl. No. 11/299,299.
Notice of Allowance and Fees Due mailed May 28, 2013 in U.S. Appl. No. 11/299,299.
Notice of Allowance and Fees Due mailed Nov. 9, 2012 in U.S. Appl. No. 11/299,299.
Non-Final Rejection mailed May 10, 2012 in U.S. Appl. No. 11/299,299.
Non-Final Rejection mailed Oct. 27, 2010 in U.S. Appl. No. 11/299,299.
Non-Final Rejection mailed Mar. 30, 2010 in U.S. Appl. No. 11/299,299.
Response mailed Aug. 6, 2012 to Office Action in U.S. Appl. No. 11/299,299.
Response mailed Jun. 9, 2011 to Office Action in U.S. Appl. No. 11/299,299.
Response mailed Jan. 7, 2011 to Office Action in U.S. Appl. No. 11/299,299.
Response mailed Aug. 2, 2010 in Office Action in U.S. Appl. No. 11/299,299.
Aug. 19, 2013 Reply to Jun. 3, 2013 Third Office Action in related Chinese Application No. 201010503565.3.
Final Office Action dated Mar. 17, 2011 in U.S. Appl. No. 11/299,299.
Advisory Action dated Jul. 22, 2011 in U.S. Appl. No. 11/299,299.
Final Rejection dated Aug. 30, 2013 in Korean Application No. 10-2007-7000514.
Atwater, H.A. "Silicon nanoparticle engineering for novel logic and memory applications" Project Overview, Functional Nanostructures Program, NSF (Jan. 2001).

(56) References Cited

OTHER PUBLICATIONS

Bell, L.D. et al., "A Radiation-tolerant, low-power non-volatile memory based on silicon nanocrystal quantum dots" Innovative Approaches to Outer Planetary Exploration 2001-2020 (Publication date unknown).
Bjork, M.T. et al. "One-dimensional steeplechase for electrons realized" Nano Letters (2002) 2:86-90.
Bodefield, M.C. et al., "Storage of electrons and holes in self-assembled InAs quantum dots" Appl. Phys. Lett. (1999) 74(13):1839-1841.
Brown, J.F. et al. "Preparation and characterization of the lower equilibrated phenylsilsesquioxanes" J. Am. Chem. Soc. (1964) 86:1120.
Brown, J.F. et al. "The polycondensation of cyclohexylsilanetriol" J. Am. Chem. Soc. (1965) 87:4313-4323.
Bulgakov, A.V. et al. "Laser ablation synthesis of zinc oxide clusters: a new family of fullerenes?" Chem. Phys. Lett. (2000) 320:19-25.
Cao, Y.W. et al. "Growth and properties of semiconductor core/shell nanocrystals with InAs cores" J. Am. Chem. Soc. (2000) 122:9692-9702.
Casperson, J.D. et al., "Materials issues for layered tunnel barrier structures" J. Appl. Phys. (2002) 92(1):261-267.
Chae, D-H et al., "Nanocrystal memory cell using high-density SiGeQuantum Dot Array" J. Kor. Phys. Soc. (1999) 35:S995-S998.
Citeau, H. et al. "A Novel cage organotellurate (IV) macrocyclic host encapsulating a bromide anion guest" Chem. Commun. (2001) pp. 2006-2007.
Coe, S. et al. "Electroluminescence from single monolayers of nanocrystals in molecular organic devices" Nature (2002) 450:800-803.
Coronado, E. et al. "Polyoxometalate-Based Molecular Materials" Chem. Rev. (1998) 98:273-296.
Corso, D. et al., "Localized Charge storage in nanocrystal memories: feasibility of a multibit cell" (Publication and Publication date unknown).
Cui, Y. et al. "Doping and electrical transport in silicon nanowires" J. Phys. Chem. B (2000) 104:5213-5216.
Cui, Y. et al. "Diameter-controlled synthesis of single-crystal silicon nanowires" Appl. Phys. Lett. (2001) 78:2214-2216.
Dabbousi, B.O. et al. "(CdSe)ZnS core-shell quantum dots: Synthesis and characterization of a size series of highly luminescent nanocrysallites" J. Phys. Chem. B (1997) 101:9463-9475.
De Blauwe, J. "Nanoparticle Nonvolatile Memory Devices," IEEE Trans. Nanotechnology (2002) 1:72.
Drexler, H. et al., "Spectroscopy of quantum levels in charge-tunable InGaAs quantum dots" Phys. Ref. Lett. (1994) 73:2252-2255.
Duan, X. et al. "General synthesis of compound semiconductor nanowires" Adv. Mater. (2000) 12:298-302.
Feher, F.J. et al. "Silsesquioxanes as models for silican surfaces" J. Am. Chem. Soc. (1989) 111:1741.
Feher, F.J. et al., "Synthesis and characterization of vanadium-containing silsesquioxanes" Inorg. Chem. (1991) 30:1689-1694.
Feher, F.J. et al. "Silsesquioxanes as ligands in inorganic and organometallic chemistry" Polyhedron (1995) 14:3239-3253.
Gigant, K. et al. "Synthesis and Molecular Structures of Some New Titanium (IV) Aryloxides" J. Am. Chem. Soc. (2001) 123:11623-11637.
Gouzerh, P. et al. "Main-group element, organic, and organometallic derivatives of polyoxometalates" Chem. Rev. (1990) 98:77-111.
Gudiksen, M.S. et al. "Diameter-selective synthesis of semiconductor nanowires" J. Am. Chem. Soc. (2000)122:8801-8802.
Gudiksen, M.S. et al. "Synthetic control of the diameter and length of single cyrstal semiconductor nanowires" J. Phys. Chem. B (2001) 105:4062-4064.
Gudiksen, M.S. et al. "Growth of nanowire superlattice structures for nanoscale photonics and electronics" Nature (2002) 415:617-620.
Hanssen, RWJM, "On the formation and reactivity of multinuclear silsesquioxane metal complexes" (2003) Dissertation Eindhoven University of Technology.
Iannaccone, G. et al., "Simulation of a quantum-dot flash memory," J. Appl. Phys. (1998) 84(9):5032-5036.
Jun, Y-W et al. "Controlled synthesis of multi-armed CdS nanorod architectures using monosurfactant system" J. Am. Chem. Soc. (2001) 123:5150-5151.
Kan, E. "Technology for self-assembled entities in logic and memory units below the lithography limit" Cornell Nanoscale Facility (Publication date unknown).
Katsoulis, D.E. "A Survey of Applications of Polyoxometalates" Chem. Rev. (1998) 98:359-387.
Kim, S-W et al. "Synthesis of monodisperse palladium nanoparticles" NanoLetters (2003) 3:1289-1291.
Kolloipoulou, S. et al., "Hybrid silicon-organic nanoparticle memory device" J. Appl. Phys. (2003) 94(8):5234-5239.
Leaustic, A. et al. "Photochromism of cationic spiropyran-doped silica gel" New J. Chem. (2001) 25:1297-1301.
Lin, Y-H et al., "High-Performance Nonvolatile HfO2 Nanocrystal Memory" IEEE Electron Device Letts (Mar. 2005) 26(3):154-156.
Liu, C. et al. "Sol-Gel Synthesis of Free-Standing Ferroelectric Lead Zirconate Titanate Nanoparticles" J. Am. Chem. Soc. (2001) 123: 4344-4345.
Liu, C-M et al. "A novel bimetallic cage complex constructed from six V4Co pentatomic rings: hydrothermal synthesis and crystal structure of [(2,2'-Py2NH)2Co]3V8O23" Chem. Commun. (2001) pp. 1636-1637.
Manna, L. et al. "Synthesis of Soluble and Processable Rod-,Arrow, Teardrop-, and Tetrapod-Shaped CdSe Nanocrystals" J. Am. Chem. Soc. (2000) 122:12700-12706.
Manna, L. et al. "Epitaxial growth and photochemical annealing of graded CdS/ZnS shells on colloidal CdSe nanorods" J. Am. Chem. Soc. (2002) 124:7136-7145.
McCarthy, W., O'Reilly Network, "Quantum Dots and Programmable Matter" (visited Jan. 12, 2004) http://www.oreillynet.com/pub/a/network/2004/01/09/quantumdots.html, 5 pages, Copyright 2000-2004 O'Reilley & Associates, Inc.
Morales, A.M. et al., "A laser ablation method for the synthesis of crystalline semiconductor nanowires" Science (1998) 279:208-211.
Muller, A. et al. "Polyoxometalates Very Large Clusters—Nanoscale Magnets" Chem. Rev. (1998) 98:239-271.
Murray, C.B. et al., "Synthesis and characterization of nearly monodisperse CdE (E=S, Se, Te) semiconductor nanocrystals" J. Am. Chem. Soc. (1993) 115:8706-8715.
Peng, X. et al. "Epitaxial growth of highly luminescent CdSe/CdS core/shell nanocrystals with photostability and electronic accessibility" J. Am. Chem. Soc. (1997) 119:7019-7029.
Peng, X. et al. "Shape control of CdSe nanocrystals" Nature (2000) 404:59-61.
Puntes, V.F. et al. "Colloidal nonocrystal shape and size control: The case of cobalt" Science (2001) 291:2115-2117.
Qu, L. et al. "Alternative routes toward high quality CdSe nanocrystals" NanoLetters (2001) 1:333-337.
Rhule, J.T. et al. "Polyoxometalates in Medicine" Chem. Rev. (1998) 98:327-357.
Appeal filed Oct. 2, 2013 in related Korean Application No. 10-2007-7000514.
Office Action dated Aug. 8, 2014 in counterpart Taiwan Patent Application No. 102120175.
Supplementary European Search Report dated Nov. 21, 2013 in counterpart European Patent Application No. EP 05784268.
Carroll et al., "Electrostatic self-assembly of structured gold nanoparticle/polyhedral oligomeric silsesquioxane (POSS) nanocomposites", Journal of Materials Chemistry, vol. 14, No. 4, Jan. 1, 2004.
Chua et al, "In Situ Characterization of Methylsilsesquioxane Curing", J. Electrochem. Soc., vol. 145, No. 11, Nov. 1, 1998.
Van Der Vlugt et al., "POSSphites-monophosphites derived from incompletely condensed silsesquioxanes", Tetrahedron Letters, Pergamon, GB, vol. 44, No. 45, Nov. 3, 2003.
Communication dated Dec. 17, 2013 in counterpart European Patent Application No. EP 05784268.
Response to Office Action filed Mar. 18, 2015 in counterpart Chinese Patent Application No. 2012103445192.
Office Action dated Sep. 3, 2014 in counterpart Chinese Patent Application No. 2012103445192.

* cited by examiner

R = alkyl, H or other atom

R = alkyl, heteroatom, or electron withdrawing group

R = alkyl, or replace OR with halide, or other leaving or binding groups

R = Isobutyl

R = Isobutyl

R = cyclohexyl where R is an alkyl group or a hydrogen atom where R is an alkyl group where R is an isobutyl group

COMPOSITIONS AND METHODS FOR MODULATION OF NANOSTRUCTURE ENERGY LEVELS

CROSS-REFERENCE TO RELATED APPLICATIONS

This application is a divisional of U.S. patent application Ser. No. 11/299,299 filed Dec. 9, 2005, which claims priority to and benefit of U.S. Provisional Patent Application Ser. No. 60/635,799, filed Dec. 13, 2004, and is a continuation-in-part of U.S. patent application Ser. No. 11/147,670, filed Jun. 7, 2005, which claims priority to and benefit of the following prior provisional patent applications: U.S. Provisional Patent Application Ser. No. 60/578,236, filed Jun. 8, 2004, U.S. Provisional Patent Application Ser. No. 60/632,570, filed Nov. 30, 2004, each of which is incorporated herein by reference in its entirety for all purposes.

BACKGROUND

The present invention is in the field of nanotechnology. More particularly, the invention is directed to ligand compositions for use in manipulating the electronic properties of nanostructure compositions (e.g., by modulating energy levels, creating internal bias fields, reducing charge transfer or leakage, etc.), as well as related methods and devices involving the ligand compositions.

Individual nanostructures, as well as those embedded in other materials to form nanocomposite materials, have many promising applications, including applications that make use of their optical and electronic properties. One particularly useful application would be in the area of nanocomposite based memory, where the nanostructures allow for high density charge storage.

Of the synthetic approaches available for preparing nanostructures, top-down patterned approaches such as chemical vapor deposition (CVD) or molecular beam epitaxy (MBE) are commonly used to generate core and core:shell nanostructures. These methods typically yield large and/or disordered and/or low density packing nanoparticles, and require high cost (high temperature, high vacuum) processing steps. Solution based syntheses can also be used to synthesize semiconductor nanocrystals (either cores or core/shells) which are more readily compatible with solution based deposition methods such as spin coating or other evaporation methods. For example, nanostructures comprising CdSe cores (or crystalline cores) with a shell of ZnS can be prepared by solution deposition techniques (see, e.g., Murray et al. "Synthesis and characterization of nearly monodisperse CdE (E=S, Se, Te) semiconductor nanocrystals" *J. Am. Chem. Soc.* 115: 8706-8715 (1993)). However, nanostructures generated by these and other standard core-shell synthetic techniques typically do not have a thick enough shell to confine a charge in the core to enough degree to prevent charge diffusion to other nanostructures placed within a few nanometers of the first nanostructure.

Alternatively, nanostructure synthesis by a chemical self-organizing approach typically produces the most well-controlled morphology and crystal size, but these synthetic protocols generate nanostructures having associated therewith additional organic and/or surfactant compounds. While useful for enhancing solubility and facilitating manipulation of the nanostructures during synthesis, the organic contaminants are avidly associated with the nanostructure surface, thus inhibiting further manipulation and/or integration of the newly synthesized nanostructure into devices and end applications.

Even if these CdSe:ZnS constructs could be prepared having diameters allowing for high density packing (e.g., about $1 \times 10^{12}/cm^2$ or greater), the ZnS shell would not provide enough quantum confinement for efficient use of the nanostructures in microelectronic and photonic devices, including, but not limited to, memory or charge storage devices.

Accordingly, there exists a need in the art for discrete coated nanostructures that can be easily integrated into various manufacturing processes without further processing. Preferably, the coated nanostructures can be closely packed while maintaining greater quantum confinement than standard CdSe/ZnS core:shell structures.

In addition, the energy levels (electron affinity) of component semiconductor materials are an important consideration for fabrication of semiconductor-containing devices, such as photovoltaic devices, memory storage devices, transistors, and light-emitting and/or light-detecting devices, such as LEDs, phosphors, photo-detectors, and the like. Bulk semiconductors have inherent valence and conduction bands associated with the specifics of the atomic composition. However, nanocrystals constructed of the same material(s) are thought to differ in energy levels compared to their bulk counterparts, due at least in part to the effects of quantum confinement; the energy levels can also be tuned for a given material, e.g., by variation of the nanocrystal size. Matching appropriate materials and energy level alignment is considered important for optimal device performance. Accordingly, there exists a need in the art for techniques that can be used to match appropriate materials and energy levels.

The present invention meets these and other needs by providing discrete coated nanostructures, ligands for coating discrete nanostructures, devices incorporating the coated nanostructures, and methods for preparing the coated nanostructures. A complete understanding of the invention will be obtained upon review of the following.

SUMMARY

The present invention relates to the manipulation of the electronic properties of a nanostructure composition through the use of an associated ligand, preferably a dipole-containing ligand. In one aspect the invention provides methods for modulating an energy level of a nanostructure in the absence of a polymeric matrix. The methods include the steps of a) providing a nanostructure having a first energy level; b) selecting a ligand composition comprising a dipole, wherein the ligand composition has a second energy level as compared to the first energy level of the nanostructure; and c) associating or coupling the ligand composition to a surface of the nanostructure, thereby modulating the energy level of the nanostructure.

In certain embodiments, the first energy level of the nanostructure and the second energy level of the ligand composition are aligned (e.g., there is no change in the band gap upon association of the ligand with the nanostructure). In an alternate embodiment, the nanostructure and ligand composition have differing energy levels. For example, for ligand compositions in which the dipole comprises an electron donating group, coupling of the ligand to the nanostructure increases the level of the highest occupied molecular orbital (HOMO). The electron donating group can comprise, for example, a conjugated aromatic phosphonic acid ligand. Alternately, for ligand compositions in which the dipole comprises an electron withdrawing moiety, the ligand composition can decrease the HOMO level. The electron withdrawing group can comprise, for example, one or more boron atoms or one or more fluorine atoms. Exemplary ligand compositions include, but are not limited to, butyl boronic acid, 4-trimethylsilylphenyl boronic acid, a carborane, a boron derivative of a polyhedral oligomeric silsesquioxane (POSS), trifluoroacetic acid, a SiF derivative, an ammonium carboxylate-modified phosphonic acid, or a spiropyran salt.

The nanostructures employed in the invention can be prepared from any of a number of materials, including semiconducting materials. Exemplary semiconducting nanostructures include, but are not limited to, nanostructures prepared using a first element selected from group II of the periodic table and a second element selected from group VI, as well as those fabricated using a first element selected from group III of the periodic table and a second element selected from group V, and nanostructures prepared using an element selected from group IV. Associating the ligand composition with the surface of the nanostructure optionally comprises performing a ligand exchange or growing the nanostructure in the presence of the ligand composition.

In a related aspect, the invention provides methods for creating an internal bias field, e.g., for extraction of electrons or holes from a nanostructure composition. The methods of the invention include the steps of a) coupling a photoactivatable composition to a surface of a nanostructure, which composition forms a dipole upon activation, and b) activating the composition (e.g., by exposing the coupled ligand:nanostructure composition to a light source) and creating the dipole, thereby forming an internal bias field. Exemplary photoactivatable compositions for use as ligands in the invention include, but are not limited to, light-activated intramolecular salts such as spiropyrans. Coupling the photoactivatable composition to the surface of the nanostructure optionally comprises performing a ligand exchange. Optionally, these methods further include the step of extracting holes or electrons from the nanostructure, e.g., by transporting the electrons or holes toward an electrode. In certain embodiments, the nanostructure is a component of a photovoltaic cell.

In a further aspect, the invention provides methods for reducing charge diffusion among a plurality of nanostructures, such as quantum dots. The methods include the steps of a) coupling a ligand composition comprising an electron withdrawing group to a surface of a member nanostructure (e.g., quantum dot), and b) forming a dipole on the surface of the member nanostructure and increasing the electron affinity of the nanostructure, thereby reducing charge diffusion among the nanostructures. Ligand compositions having electron withdrawing characteristics that can be used in the methods include, but are not limited to, fluorine-containing compositions (e.g., $F^-SiF$ and derivatives, fluorine polymers such as polytetrafluoroethylene, etc.), boron-containing compositions (e.g., aryl-boron oligomers and boronic acid compositions), light-activated intramolecular salts such as spiropyrans, and silicon oxide cage complexes such as silsesquioxanes. Preferably, the ligand composition includes a phosphonic acid moiety or other nanostructure binding moiety. The methods are particularly useful in the preparation and use of nanostructures, particularly quantum dots, for use in media utilized for discrete quantized photon (or charge) generation and/or transfer.

The invention also provides ligand compositions for modulating nanostructure energy levels. In one class of embodiments, ligand compositions of the invention include a nonconjugated body structure having a dipole moiety, and a nanostructure binding moiety coupled to the nonconjugated body structure at a first position. Optionally, the nonconjugated body structure includes a second dipole coupled at a second position. Exemplary nonconjugated body structures for use in the ligand compositions include, but are not limited to, fluorine-containing compositions such as those noted above, carboranes and other boron-containing compositions, and light activated intramolecular salts. Exemplary nanostructure binding moieties include, but are not limited to, phosphonic acid, carboxylic acid, amine, phosphine, and thiol moieties.

In another class of embodiments, ligand compositions for modulating nanostructure energy levels have a body structure comprising a light-activated spiropyran salt and a nanostructure binding moiety coupled to the body structure at a first position. Exemplary nanostructure binding moieties include, but are not limited to, phosphonic acid, carboxylic acid, amine, phosphine, and thiol moieties.

In a further class of embodiments, ligand compositions for modulating nanostructure energy levels comprise a body structure comprising a boron-containing oligomer and a nanostructure binding moiety coupled to the body structure at a first position. The boron-containing oligomers optionally are an $(AB)_n$ composition, wherein A is an aryl (or other conjugated) moiety and B is a boron atom. In some embodiments, the boron atoms are positioned para to one another, while in other embodiments, the positioning is meta.

In yet another class of embodiments, ligand compositions for modulating nanostructure energy levels comprise a body structure comprising a thiophene moiety and a nanostructure binding moiety coupled to the body structure at a first position. The composition optionally includes a boron atom, e.g., as part of the nanostructure binding moiety (e.g., as part of a boronic acid group).

Nanostructure compositions (e.g., nonpolymeric compositions) comprising a plurality of nanostructures having coupled thereto a plurality of a selected ligand composition are also a feature of the invention, as are devices including such nanostructure compositions.

These and other objects and features of the invention will become more fully apparent when the following detailed description is read in conjunction with the accompanying figures.

DEFINITIONS

Before describing the present invention in detail, it is to be understood that this invention is not limited to particular devices or systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a nanostructure" includes a combination of two or more nanostructures; reference to "a ligand composition" includes mixtures of ligands; reference to "a substituent" includes mixtures of substituents, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The term "nanostructure" as used herein refers to a structure having at least one region or characteristic dimension having a dimension of less than about 500 nm, e.g., less than about 100 nm, less than about 50 nm, or even less than about 10 nm or about 5 nm. Typically, the region or characteristic dimension will be along the smallest axis of the structure. Examples of such structures include nanowires, nanorods, nanotubes, branched nanocrystals, nanotetrapods, tripods, bipods, nanocrystals, nanodots, quantum dots, nanoparticles, branched tetrapods (e.g., inorganic dendrimers), and the like. Nanostructures can be substantially homogeneous in material properties, or in certain embodiments can be heterogeneous (e.g., heterostructures). Nanostructures can be, e.g., substantially crystalline, substantially monocrystalline, polycrystalline, metallic, polymeric, amorphous, or a combination thereof. The nanostructures can comprise, e.g., a metal, semiconductor, insulator, or a combination thereof. In one aspect, each of the three dimensions of the nanostructure has a dimension of less than about 500 nm, e.g., less than about 200 nm, less than about 100 nm, less than about 50 nm, less than about 10 nm, or even less than about 5 nm.

The terms "crystalline" or "substantially crystalline," when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. In some instances, a nanostructure can bear an oxide or other coating, or can be comprised of a core and at least one shell. In such instances it will be appreciated that the oxide, shell(s), or other coating need not exhibit such ordering (e.g., it can be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein.

The term "monocrystalline" when used with respect to a nanostructure indicates that the nanostructure is substantially crystalline and comprises substantially a single crystal. Then used with respect to a nanostructure heterostructure comprising a core and one or more shells, "monocrystalline" indicates that the core is substantially crystalline and comprises substantially a single crystal.

A "nanocrystal" is a nanostructure that is substantially monocrystalline. A nanocrystal thus has at least one region or characteristic dimension with a dimension of less than about 500 nm, e.g., less than about 200 nm, less than about 100 nm, less than about 50 nm, or even less than about 20 nm. The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. In one aspect, each of the three dimensions of the nanocrystal has a dimension of less than about 500 nm, e.g., less than about 200 nm, less than about 100 nm, less than about 50 nm, or even less than about 20 nm. Examples of nanocrystals include, but are not limited to, substantially spherical nanocrystals, branched nanocrystals, and substantially monocrystalline nanowires, nanorods, nanodots, quantum dots, nanotetrapods, tripods, bipods, and branched tetrapods (e.g., inorganic dendrimers).

A "substantially spherical nanocrystal" is a nanocrystal with an aspect ratio between about 0.8 and about 1.2.

A "nanorod" is a nanostructure that has one principle axis that is longer than the other two principle axes. Consequently, the nanorod has an aspect ratio greater than one. Nanorods of this invention typically have an aspect ratio between about 1.5 and about 10, but can have an aspect ratio greater than about 10, greater than about 20, greater than about 50, or greater than about 100, or even greater than about 10,000. Longer nanorods (e.g., those with an aspect ratio greater than about 10) are sometimes referred to as nanowires. The diameter of a nanorod is typically less than about 500 nm, preferably less than about 200 nm, more preferably less than about 150 nm, and most preferably less than about 100 nm, about 50 nm, or about 25 nm, or even less than about 10 nm or about 5 nm. Nanorods can have a variable diameter or can have a substantially uniform diameter, that is, a diameter that shows a variance less than about 20% (e.g., less than about 10%, less than about 5%, or less than about 1%) over the region of greatest variability. Nanorods are typically substantially crystalline and/or substantially monocrystalline, but can be, e.g., polycrystalline or amorphous.

A "branched nanostructure" is a nanostructure having three or more arms, where each arm has the characteristics of a nanorod, or a nanostructure having two or more arms, each arm having the characteristics of a nanorod and emanating from a central region that has a crystal structure distinct from that of the arms. Examples include, but are not limited to, nanobipods (bipods), nanotripods (tripods), and nanotetrapods (tetrapods), which have two, three, or four arms, respectively.

A "nanotetrapod" is a generally tetrahedral branched nanostructure having four arms emanating from a central region or core, where the angle between any two arms is approximately 109.5 degrees. Typically, the core has one crystal structure and the arms have another crystal structure.

A "nanoparticle" is any nanostructure having an aspect ratio less than about 1.5. Nanoparticles can be of any shape, and include, for example, nanocrystals, substantially spherical particles (having an aspect ratio of about 0.9 to about 1.2), and irregularly shaped particles. Nanoparticles can be amorphous, crystalline, partially crystalline, polycrystalline, or otherwise. Nanoparticles can be substantially homogeneous in material properties, or in certain embodiments can be heterogeneous (e.g., heterostructures). The nanoparticles can be fabricated from essentially any convenient material or materials.

An "aspect ratio" is the length of a first axis of a nanostructure divided by the average of the lengths of the second and third axes of the nanostructure, where the second and third axes are the two axes whose lengths are most nearly equal each other. For example, the aspect ratio for a perfect rod would be the length of its long axis divided by the diameter of a cross-section perpendicular to (normal to) the long axis.

As used herein, the "diameter" of a nanostructure refers to the diameter of a cross-section normal to a first axis of the nanostructure, where the first axis has the greatest difference in length with respect to the second and third axes (the second and third axes are the two axes whose lengths most nearly equal each other). The first axis is not necessarily the longest axis of the nanostructure; e.g., for a disk-shaped nanostructure, the cross-section would be a substantially circular cross-section normal to the short longitudinal axis of the disk. Where the cross-section is not circular, the diameter is the average of the major and minor axes of that cross-section. For an elongated or high aspect ratio nanostructure, such as a nanowire or nanorod, a diameter is typically measured across a cross-section perpendicular to the longest axis of the nanowire or nanorod. For spherical nanostructures such as quantum dots, the diameter is measured from one side to the other through the center of the sphere.

As used herein, the term "coating" refers to a ligand that has been applied to a surface, such as the surface of a nanostructure. The coating either can fully or partially encapsulate the structure to which it has been applied. Furthermore, the coating can be porous or solid.

The term "optical property" refers to physical characteristics involving the transmission or generation of photons.

Likewise, the term "electrical property" refers to refers to physical characteristics involving the transmission or generation of electrons (or holes).

The phrases "high density packing" or "high density" refer to densities of about $10^{12}$ nanostructures per $cm^2$ or greater.

An "organic group" is a chemical group that includes at least one carbon-hydrogen bond.

A "hydrocarbon group" is a chemical group consisting of carbon and hydrogen atoms.

An "alkyl group" refers to a linear, branched, or cyclic saturated hydrocarbon moiety and includes all positional isomers, e.g., methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, cyclopentyl, cyclohexyl, n-heptyl, n-octyl, 2-ethylhexyl, n-nonyl, n-decyl and the like. Alkyl groups can be, e.g., substituted or unsubstituted.

An "alkenyl group" refers to a linear, branched, or cyclic unsaturated hydrocarbon moiety that comprises one or more carbon-carbon double bonds. Exemplary alkenyl groups include ethenyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-2-propenyl, and the like. Alkenyl groups can be substituted or unsubstituted.

An "alkynyl group" refers to a linear, branched, or cyclic unsaturated hydrocarbon moiety that comprises one or more carbon-carbon triple bonds. Representative alkynyl groups include, e.g., 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl 1-ethyl-1-methyl-2-propynyl, and the like. Alkynyl groups can be substituted or unsubstituted.

The term "aryl group" refers to a chemical substituent comprising or consisting of an aromatic group. Exemplary aryl groups include, e.g., phenyl groups, benzyl groups, tolyl groups, xylyl groups, alkyl-aryl groups, or the like. Aryl groups optionally include multiple aromatic rings (e.g., diphenyl groups, etc.). The aryl group can be, e.g., substituted or unsubstituted. In a "substituted aryl group", at least one hydrogen is replaced with one or more other atoms.

The term "alkyl-aryl group" refers to a group that comprises alkyl and aryl moieties.

A "heteroatom" refers to any atom which is not a carbon or hydrogen atom. Examples include, but are not limited to, oxygen, nitrogen, sulfur, phosphorus, and boron.

A "surfactant" is a molecule capable of interacting (whether weakly or strongly) with one or more surfaces of a nanostructure.

The term "about" as used herein indicates the value of a given quantity varies by +/−10% of the value, or optionally +/−5% of the value, or in some embodiments, by +/−1% of the value so described.

A variety of additional terms are defined or otherwise characterized herein.

DETAILED DESCRIPTION

Figure 1:
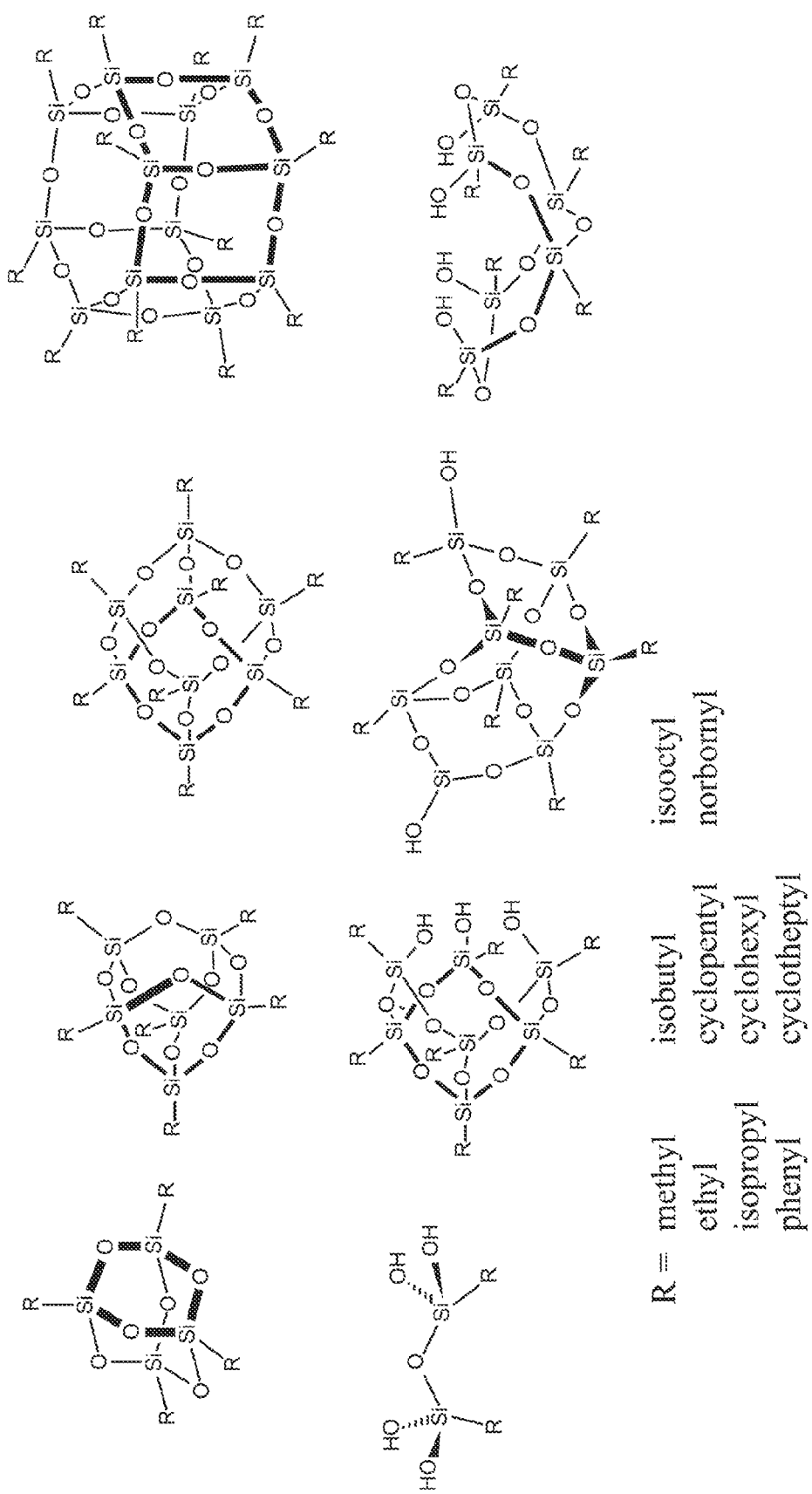
FIG. 1 depicts exemplary silsesquioxane frameworks for use as nanostructure ligands in the present invention.

Many electronics applications would benefit from processes and compositions that provided nanostructures having improved energy barrier heights and/or quantum confinement. Nanostructures having these enhanced properties could be used, e.g., for quantized charge storage and/or transfer in the field of microelectronics, or for photon generation and transfer in photonics. For example, solid state storage devices such as flash memory devices use storage media having discrete read and write properties. Enhanced storage capacities could be implemented by storing charge on densely-packed discrete nanostructures, such as quantum dots. In particular, nanostructures that pack well at high density (e.g., those having spherical, nearly spherical, and/or isotropic structures, such as nanodots or quantum dots) as well as improved quantum confinement properties are particularly promising for use in discrete and/or quantized charge storage, as well as for photon generation and transfer.

Cross-talk between dots (i.e., signal interference due to electronic interactions between the nanostructures) leads to poor device performance. The present invention, however, provides compositions, methods and devices in which nanostructured charge storage elements are able to be closely packed (e.g., at densities of 1×10$^{10}$/cm$^2$ or greater, even at a high density, e.g., at 1×10$^{12}$/cm$^2$ or greater), while preserving or improving quantum confinement, either by controlling the distance between the nanostructures and/or by introducing an insulating or dielectric coating material such as silicon dioxide around discrete nanostructures.

For example, two significant issues considered with respect to the use of nanostructures as charge storage elements are the inclusion of appropriate surface properties, and the packing of the selected nanostructures into ordered or disordered monolayers. For high-density data storage applications, the nanostructures are preferably provided as one or more close-packed ordered monolayers. In the case of semiconducting nanocrystals, hexagonally packed monolayers of CdSe have been prepared in the art by making use of phase segregation between aliphatic surfactants on the nanocrystals and aromatic conjugated organic materials, and deposition via spin-coating. However, the embedding of nanocrystals into (or on top of) an organic matrix is not desirable in memory device fabrication processes. To this end, the present invention provides, in one embodiment, monolayers of quantum dots with silsesquioxane or silicate ligand surface ligands prepared by various self-assembly methods and compatible with charge storage applications.

Maintaining a selected distance between nanostructures can be achieved using a ligand or coating associated with the nanostructure surface. The size of the ligand-nanostructure complex, and thus the distance between adjacent nanostructures, can be varied for different applications by altering the composition of the associated ligand. Thus, the size of the ligand can be used to control dot-to-dot spacing during the preparation of a nanostructure-containing substrate or matrix.

In addition, the physical properties of the nanostructure composition can also be adjusted by introducing a ligand coating that can be converted to a second coating having a second, desired property (for example, being dielectric). For example, in some embodiments provided herein, the coated nanocrystals in their "post-processing" or cured state are insulated with silicon dioxide-containing second coatings or shells, e.g., to reduce cross-talk between nanocrystals. Other desirable properties include, but are not limited to, malleability, rigidity, thermal tolerance, conductivity, transparency, and opaqueness (opacity), depending upon the application involved. Furthermore, ligand compositions that, upon conversion to a second coating, affect the HOMO or valence bond levels of the nanostructure composition are also included in the compositions of the present invention.

One general class of embodiments provides a discrete coated nanostructure. The discrete coated nanostructure includes an individual nanostructure having a first surface, and a first coating associated with the first surface of the individual nanostructure. The first coating has a first optical, electrical, physical or structural property, and is capable of being converted to a second coating having one or more of a different optical, electrical, physical or structural property than the first coating. In some embodiments, the first coating encapsulates the nanostructure; in other embodiments, the first coating covers a portion of the nanostructure (for example, the portion of the nanostructure not associated with the surface of a substrate). In one embodiment, the electrical property of the second coating is a dielectric property; exemplary second coatings for this embodiment include silicon oxide, boron oxide, and combinations thereof.

Nanostructures that can be used to prepare the discretely coated composition of the present invention include, but are not limited to, nanocrystals, nanodots, nanowires, nanorods, nanotubes, various nanoparticles, including, e.g., metal, semiconductor, or insulator nanoparticles, metal nanoparticles such as palladium, gold, platinum, silver, titanium, iridium, cobalt, tin, zinc, nickel, iron or ferrite nanoparticles or alloys of these, amorphous, crystalline, and polycrystalline inorganic or organic nanoparticles, and polymeric nanoparticles, such as those typically used in combinatorial chemical synthesis processes, e.g., like those available from Bangs Laboratories (Fishers, Ind.), nanotetrapods, nanotripods, nanobipods, branched nanostructures, branched nanocrystals, and branched tetrapods. In a preferred embodiment, the nanostructure comprises a spherical, nearly spherical, and/or isotropic nanoparticle such as a nanodot and/or a quantum dot. Preferably, the coated nanostructure has at least one dimension (for example, a diameter of the coated nanostructure) that is less than about 10 nm, and optionally less than about 8 nm, 5 nm, or 4 nm. In some embodiments of the present invention, the diameter of the coated nanostructure is between about 2 nm and about 6 nm, e.g., between 2-4 nm.

A number of ligand compositions can be employed as coatings for the nanostructure. In one class of embodiments, the second coating comprises an oxide (e.g., SiO$_2$). In some embodiments, the first coating has a first component comprising a silicon oxide cage complex and a second component comprising one or more nanostructure binding moieties. Exemplary nanostructure binding moieties include either the protonated or deprotonated forms of phosphonate, phosphinate, carboxylate, sulfonate, sulfinate, amine, alcohol, amide, and/or thiol moieties. Preferred nanostructure binding moieties include ester moieties of phosphonate, phosphinate, carboxylate, sulfonate, and sulfinate. Typically, the nanostructure binding moieties are independently coupled to the silicon oxide cage complex, e.g., via an oxygen or silicon atom of the cage.

In certain embodiments, the coated nanostructure includes a silsesquioxane composition as the first coating. The silsesquioxane can be either a closed cage structure or a partially open cage structure. Optionally, the silicon oxide cage complex (e.g., the silsesquioxane) is derivatized with one or more boron, methyl, ethyl, branched or straight chain alkanes or alkenes with 3 to 22 (or more) carbon atoms, isopropyl, isobutyl, phenyl, cyclopentyl, cyclohexyl, cycloheptyl, isooctyl, norbornyl, and/or trimethylsilyl groups, electron withdrawing groups, electron donating groups, or a combination thereof. In an alternate embodiment, discrete silicates are employed in the first coating composition. One discrete silicate which can be used as first coatings is phosphosilicate. Upon curing, the silicon oxide cage complex first coating is typically converted to a second rigid coating comprising a silicon oxide (e.g., $SiO_2$).

The coatings employed in the compositions of the present invention typically exhibit a first property in their initial (i.e., pre-conversion or pre-cured) state, and a second, differing property in the second, post-conversion or post-curing state. For examples involving coatings having differing electrical properties upon conversion or curing, the first electrical property could include conductivity while the second electric property is nonconductivity (or vice versa). Likewise, the material in the first state may be an electron conductor or a neutral material, while the material in the second state may be a hole conductor. Alternatively, for embodiments relating to optical properties, the first and second optical properties could be opacity and transparency, e.g., to visible light. Alternatively, the first optical property could include light absorption (or transmission or emission) at a first wavelength, while the second optical property comprises light absorption (or transmission or emission) at a second wavelength. Alternatively, for embodiments relating to structural properties, the material in the first state could be a flexible molecule, while the second state could comprise a rigid (porous or solid) shell. In one class of embodiments, the first physical property comprises solubility, e.g., in a selected solvent, while the second electrical property comprises nonconductivity. Conversion of the coating can be accomplished, e.g., by application of heat and/or radiation.

The present invention also provides an array comprising a plurality of discrete coated nanostructures. In a preferred embodiment, the member nanostructures are present at a density greater than about $1\times10^{10}/cm^2$, greater than about $1\times10^{11}/cm^2$, and more preferably at greater than about $1\times10^{12}/cm^2$ or even greater than about $1\times10^{13}/cm^2$. Optionally, the member nanostructures are associated with a surface of a substrate, such as a silicon wafer. In some embodiments, the member nanostructures are encapsulated prior to association with the substrate surface, while in other embodiments, a first portion of a member nanostructure is associated with the substrate, and a second portion of the member nanostructure is associated with the first coating or the second coating. Optionally, the surface of the substrate includes a surface-binding ligand coupled to a second nanostructure binding moiety, e.g., for association with a portion of the nanostructure surface. For example, in the case of a silicon wafer, a silane moiety would function as the binding ligand on the substrate or surface.

Devices including a plurality of discrete coated nanostructures form another feature of the invention. Exemplary devices that can incorporate the discrete coated nanostructures of the invention include, but are not limited to, a charge storage device, a memory device (e.g., a flash memory device), and a photovoltaic device.

In another aspect, the present invention provides a coated nanostructure-containing composition having a plurality of nanostructures and a coating separating each member nanostructure. The coating includes a plurality of nanostructure binding moieties attached to a surface of the member nanostructure; after association of the nanostructure binding moieties with the surface of the member nanostructure, the coating can be converted to the second coating (e.g., an insulating shell; the first coating is optionally also insulating). Optionally, the second coating or "shell" is an inflexible structure that provides a spacing (e.g., a selected or defined distance, or rigid spacing) between adjacent member nanostructures. For example, depending upon the coating employed, the diameter of a given coated nanostructure (or the distance from center to center between adjacent nanostructures in a packed array) can range, e.g., between about 1 and about 100 nm, or optionally between about 1 nm and about 50 nm. In preferred aspects, a higher packing density is desired, and thus a distance between nanostructures optionally ranges from about 1 nm to about 10 nm, about 3 nm to about 10 nm, and more preferably, between about 2 nm and about 6 nm, e.g., between about 3 and about 5 nm or about 2 nm and about 4 nm. In certain aspects for which a thickness that provides acceptable insulation or coating thickness while preserving a high packing density is preferred, the diameter of the coated nanostructure falls within a range of from about 2 nm to about 6 nm, or optionally about 3.5 nm (or less).

In some embodiments, the insulating shell reduces or prevents (e.g., lateral) charge diffusion or transmission between adjacent or proximal member nanostructures, or between a nanostructure and another adjacent or proximal material or substrate. Alternatively, the shell may reduce or prevent other types of transmission, such as light or heat. In one class of embodiments, the insulating shell reduces the rate of charge diffusion between member nanostructures, whereby the average time for an electron to hop from one member nanostructure to another is greater than a predetermined length of time (e.g., greater than 1 millisecond, 1 second, 1 minute, 1 hour, 1 day, 1 month, or even 1 year or more).

The member nanostructures can be associated with a surface of a substrate. In one class of embodiments, the substrate comprises a silicon substrate. The silicon substrate can comprise a functionalized or oxidized silicon substrate. In one class of embodiments, the silicon substrate further comprises a silane ligand coupled to a second nanostructure binding moiety. The plurality of nanostructure binding moieties and the second nanostructure binding moiety can be similar chemical moieties, or they can be disparate chemical moieties.

Nanostructure binding moieties that can be employed in the compositions of the present invention include, but are not limited to, one or more phosphonate ester, phosphonic acid, carboxylic acid or ester, amine, phosphine, phosphine oxide, sulfonate, sulfinate, alcohol, epoxide, amide or thiol moieties. The coating used to form the insulating shell can be an organic, an inorganic, or a hybrid organic/inorganic composition. In some embodiments of the present invention, the nanostructure-binding coating comprises a silicon oxide cage complex, such as one or more silsesquioxanes or discrete silicates.

Essentially all of the features described for the embodiments above apply to these embodiments as well, as relevant; for example, with respect to type of nanostructures, density of member nanostructures, association with a substrate, inclusion in devices, and/or the like. The composition optionally includes a topcoat composition, e.g., one comprising the same material as the coating or the insulating shell.

In a further embodiment, the present invention also provides a plurality of discrete nanostructures encompassed with rigid $SiO_2$ shells, wherein a diameter of a member nanostructure:shell construct (i.e., a member nanostructure with its shell) is less than about 10 nm (or optionally less than about 8 nm, less than about 6 nm, less than about 4 nm, or less than about 3.5 nm), and/or wherein the member nanostructures are present at a density greater than $1\times10^{10}/cm^2$, or optionally greater than about $1\times10^{11}/cm^2$, about $1\times10^{12}/cm^2$, or even equal to or greater than about $1\times10^{13}/cm^2$. The member nanostructures are optionally arranged in an array, e.g., an ordered or disordered array. Essentially all of the features described for the embodiments above apply to these embodiments as well, as relevant; for example, with respect to type of nanostructures, association with a substrate, inclusion in devices, topcoats, and/or the like.

In one class of embodiments in which the plurality of discrete nanostructures are encompassed with rigid $SiO_2$ shells, a diameter of a member nanostructure with its shell is less than about 6 nm, and the member nanostructures are present at a density greater than $1\times10^{12}/cm^2$, the member nanostructures are associated with a surface of a substrate. The plurality of nanostructures can further comprise a top coating. The top coating optionally comprises a silicon oxide top coating.

The present invention also provides devices, systems, compositions, films, and the like having therein a plurality of discrete coated nanostructures. One exemplary device that could be used with the discrete coated nanostructures of the present invention is a memory device, e.g., a flash memory device. In a preferred embodiment, the flash memory device includes a plurality of discrete nanostructures encompassed with rigid $SiO_2$ shells, wherein a diameter of a member nanostructure is less than about 6 nm, and wherein the member nanostructures are present at a density greater than about $1\times10^{10}/cm^2$, or more preferably, densities greater than about $1\times10^{12}/cm^2$. Other exemplary devices include charge storage devices and photovoltaic devices.

In a further aspect, the present invention provides methods for post-deposition shell formation on a nanostructure. The methods include the steps of providing one or more nanostructures having a ligand composition associated with a first surface, which ligand composition is capable of being converted to a rigid shell, and converting or curing the ligand composition and generating the rigid shell on the first surface of the nanostructure, thereby forming the shell after deposition of the ligand composition. The ligand composition can be, e.g., any of those described herein.

In one class of embodiments, the ligand composition comprises a plurality of nanostructure binding moieties coupled to a silicon oxide cage complex. The silicon oxide cage complex can comprise a silsesquioxane composition. In one class of embodiments, the rigid shell comprises an electrically conductive composition. In one class of embodiments, the rigid shell comprises an electrically insulating composition. In one class of embodiments, the rigid shell comprises an optically transparent composition.

The nanostructures can be provided by synthesizing one or more nanowires, nanorods, nanotubes, branched nanostructures, branched nanocrystals, nanotetrapods, nanotripods, nanobipods, nanocrystals, nanodots, quantum dots, nanoparticles, or branched tetrapods (or a combination thereof) by any of a number of techniques known in the art. For some embodiments, providing the one or more nanostructures involves providing semiconductor nanocrystals or metal nanocrystals having at least one dimension of less than 10 nm, less than about 5 nm, or between 2-4 nm or smaller.

In one class of embodiments, the nanostructures having a ligand composition associated with a first surface are provided by providing one or more nanostructures having one or more surfactants associated with the first surface and exchanging the surfactants with the ligand composition. The step of exchanging the surfactants can be achieved by various procedures. For example, the surfactants (e.g., carboxylic acids, fatty acids, phosphines and/or phosphine oxides) can be exchanged via a "mass action" effect, by suspending or dissolving the nanostructures in an organic solvent and combining the suspended nanostructures with the ligand composition, thereby exchanging the surfactants on the first surface with the ligand composition. Organic solvents that can be employed for this step include, but are not limited to, toluene, chloroform, chlorobenzene, and combinations thereof. Alternatively, the surfactants can be removed in situ (e.g., after deposition on a substrate) by various techniques, such as performing a low temperature organic stripping procedure followed by oxidation using a reactive oxygen species (provided, e.g., by UV ozone generation, RF monoatomic oxygen generation, or oxygen radical generation). The ligand composition can then be associated with the stripped nanostructures. In an alternative class of embodiments, the nanostructures are synthesized in the presence of the ligand composition, and thus no surfactant exchange step is required.

The methods of the present invention include the step of converting or curing the ligand composition to generate a second coating (e.g., in some embodiments, a rigid and/or insulating shell) on the first surface of the ligand-exchanged nanostructure. In a preferred embodiment, the curing step is performed by heating the nanostructure having the ligand composition associated therewith at temperatures that will not degrade or otherwise compromise the nanostructure. For the nanostructure-containing compositions of the present invention, curing is typically achieved at temperatures less than about 500° C. In some embodiments, the heating process is performed between 200-350° C. The curing process results in the formation of the second coating or shell (e.g., a thin, solid matrix on the first surface of the nanostructure). The shell can comprise, for example, an electrically conductive composition, an electrically insulating composition, an optically transparent composition, an optically opaque composition, or even a combination of these features. In a preferred embodiment, the second coating is a rigid insulating shell comprising a glass or glass-like composition, such as $SiO_2$. The curing step is optionally performed by heating the nanostructure in an oxidizing atmosphere.

Optionally, the nanostructures employed in the methods of the present invention are coupled to a substrate, e.g., via a second nanostructure surface. While various substrates can be employed, one exemplary substrate is a silicon substrate, e.g., a silicon wafer (e.g., with or without a silicon oxide coating). Another exemplary substrate is a silicon nitride surface, either on a silicon wafer, transmission electron microscope (TEM) grid, or other suitable substrate. In some embodiments, coated nanostructures are coupled via a second nanostructure surface (e.g., a portion of the surface not in contact with the ligand composition).

Optionally, the methods of the present invention further include the step of applying a planarization composition, e.g., a spin-on glass planarization composition, to the one or more nanostructures coupled to a substrate. While this optional step can be performed either prior to or after the curing step, the planarization composition is preferably applied after curing of the ligand into the rigid shell.

In a further aspect, the present invention provides nanostructures having a rigid shell formed post-deposition as prepared by the methods described herein. In some preferred embodiments, the rigid shell comprises silicon (for example, $SiO_2$) and/or boron (e.g., $B_2O_3$). The rigid shell can comprise silicon or silicon oxide. In one class of embodiments, the rigid shell is a rigid dielectric coating, and the ligand composition used to prepare the rigid shell comprises a) a first component comprising a silicon oxide cage complex, and b) a second component comprising one or more nanostructure binding moieties, wherein each nanostructure binding moiety is independently coupled to the silicon oxide cage complex. Each nanostructure binding moiety is optionally independently coupled to the silicon oxide cage complex via an oxygen atom. A diameter of the nanostructure is optionally less than 6 nm, e.g., less than 3.5 nm.

However, while primarily described in terms of charge insulation and/or nanostructure spacing for, e.g., charge storage applications such as non-volatile memory, it will be appreciated by those of skill in the art upon reading the present disclosure that the present invention, and or various individual or combined component aspects thereof, possess far broader applicability than that which is embodied by these specific applications. In particular, the ability to provide or include a convertible coating that can be converted in situ, or otherwise when desired (e.g., after association with the nanostructure, so as to alter the property of the nanostructure), has broadly applicable value. For example, optical coatings may be deposited using a coating material that offers a first optical property, but which may be converted to a second optical property, post-deposition. Additionally, the ability to individually associate a coating with a nanostructure, which coating may be more easily manipulated in one form, but may be later converted while already uniformly or otherwise desirably coated onto the nanostructure, provides significant advantages to previously described nanostructure coating processes.

Other aspects of the present invention provide ligand compositions for use in manipulating the electronic properties of nanostructures, for example, by modulating energy levels, creating internal bias fields, or reducing charge transfer or leakage. Such ligand compositions are optionally, but need not be, convertible coatings such as those noted above. Methods and devices related to the ligand compositions for modulating nanostructure energy levels are also described, as are nanostructures associated with the ligands.

Discrete Coated Nanostructures

The present invention provides methods and compositions involving discrete coated nanostructures. These nanostructures differ from nanostructures embedded in a matrix, in that each coated nanostructure has, upon synthesis or after subsequent application, a defined boundary provided by the coating that is not contiguous with the surrounding matrix. For ease of discussion, the coating material is generally referred to herein as a "ligand" in that such coating typically comprises molecules that have individual interactions with the surface of the nanostructure, e.g., covalent, ionic, van der Waals, or other specific molecular interactions. The present invention also provides a plurality of discrete coated nanostructures, in which the first coatings have been converted to the second coatings such that the individual nanostructures are not in direct contact or otherwise in undesirable communication, e.g., electrical communication. Furthermore, the second coating (shell) component of the coated nanostructure is often non-crystalline, unlike the typical core:shell type nanostructures known in the art. Optionally, the diameters of the coated nanostructures (e.g., the nanostructure:coating construct) are less than about 10 nm, and optionally less than about 5 nm, less than about 4 nm, or even less than about 3.5 nm.

A discrete coated nanostructure of the present invention includes an individual nanostructure having a first surface and a first coating associated with the first surface of the individual nanostructure and having a first optical, electrical, physical or structural property, wherein the first coating is capable of being converted to a second coating having a different electrical, optical, structural and/or other physical property than the first coating. In some embodiments, the first coating encapsulates the nanostructure (i.e., it completely surrounds the nanostructure being coated). In other embodiments, the nanostructure is partially encapsulated. For example, the first coating can cover the portion of the nanostructure not associated with another composition, such as the surface of a substrate.

Pluralities of Coated Nanostructures

The present invention also provides a coated nanostructure-containing composition having a plurality of nanostructures having a first coating separating each member nanostructure. Typically the coating has a plurality of nanostructure binding moieties that are employed to attach the coating to the surface of the member nanostructures. The first coating then can be converted to a second coating or shell that possesses at least one different property from the original coating, e.g., a coating that is electrically, optically, chemically, and/or structurally different, e.g., insulative as opposed to conductive (or at least non-insulative), or rigid instead of malleable. An insulating coating (or insulating shell) as described herein comprises a material that is nonconductive (e.g., dielectric). An insulating shell is generally capable of preventing substantial charge transfer for at least a brief length of time; for example, the insulating shell can reduce the rate of charge diffusion between member nanostructures, such that the average time for an electron to hop from one member nanostructure to another is at least a millisecond, or optionally at least 10 milliseconds, at least 100 milliseconds, at least 1 second, at least 1 minute, at least 1 hour, at least 1 day, at least 1 month, or at least 1 year or longer. Optionally, the charge transfer is substantially prevented (e.g., a device comprising the insulated nanostructures can maintain an applied charge) for a predetermined length of time ranging from 1 millisecond to at least 1 second, 1 minute, 1 hour, 1 day, 1 year, or longer. By providing a convertible coating mechanism in accordance with the present invention, e.g., as opposed to a synthesized nanocrystal that includes a shell component, one can garner a number of advantages, including, e.g., providing smaller core-shell structures, and potentially more coherent shell layers, that allow higher packing densities when such nanocrystals are arranged in a layer, e.g., a monolayer. For some embodiments, providing the plurality of nanostructures at a density of about $1 \times 10^{10}/cm^2$ is sufficient. However, in preferred embodiments, the plurality of nanostructures in the nanostructure-containing composition layer are present at a density of about $1 \times 10^{11}/cm^2$ or greater, or about $1 \times 10^{12}/cm^2$ or greater, and more preferably, at about $1 \times 10^{13}/cm^2$ or greater.

Optionally, the plurality of discrete coated nanostructures (e.g., at a selected density) are provided as a monolayer. However, in some embodiments, the plurality of nanostructures includes multiple monolayers, each independently having a selected or desired density of member nanostructures.

In a preferred embodiment, the plurality of coated nanostructures function as charge storage elements in various high-density data storage applications. Two key requirements for the use of the plurality of coated nanostructures in these applications are the selection of appropriate surface properties, and close packing of the nanostructures in monolayer arrays, optionally well-ordered monolayer arrays. As shown by Bulović and coworkers (Coe et al. "Electroluminescence from single monolayers of nanocrystals in molecular organic devices" Nature 420:800-803 (2002)), hexagonally-packed monolayers of CdSe-type semiconducting nanocrystals can be prepared by taking advantage of phase segregation between aliphatic surfactants on the nanocrystals and aromatic conjugated organic materials deposited on the nanocrystal via spin-coating. However, a composition of nanocrystals embedded into (or on top of) a 40 nm thick organic matrix is not desirable in memory device fabrication processes. Among other issues, the thickness of the (fairly-conductive) organic matrix will not provide enough quantum confinement, and will reduce the read/write efficacy and predictability of the device. Furthermore, the organic layer(s) are not compatible with typical memory fabrication techniques. To this end, coated nanostructures which are more compatible with charge storage applications are provided by the present invention. In a specific preferred embodiment, the plurality of coated nanostructures of the present invention comprise one or more monolayers of nanodots having silsesquioxane or silicate ligand surface ligands. These can be prepared, for example, by various self-assembly methods as described herein; after curing, the resulting nanostructures are insulated by the second coating of silicon dioxide-containing ligands. Among other advantages, the oxide second coating reduces cross-talk between nanostructures.

Coatings and Related Properties

The ligands employed as first coatings in the compositions, devices and methods of the present invention are prepared as a means by which to generate a second coating having a selected or desired property (or properties). The second coating provides an altered electrical, optical, physical or structural state as compared to the first coating, such as changes in rigidity, solubility, and/or in optical properties (refractive index, emission and/or absorption properties). A variety of coating compositions are considered for use in the present invention. For example, the coating can be an organic composition, such as various polymeric precursors that may be chemically or radiatively converted to altered (second) coating compositions, e.g., through cross-linking, further polymerization, etc. Exemplary organic compositions include, but are not limited to, dendrimer PAMAM (amine dendrimer), amine-(or other nanocrystal binding head group) terminated methyl methacrylate (polymethylmethacrylate precursor), phosphonate head group-containing polymers, carboxylic acid-terminated diene or diacetylene compositions, any heteroatom containing monomer(s) that can be converted to polymers upon chemical, heat or light activation, as well as the ligands described in by Whiteford et al. U.S. patent application Ser. No. 10/656,910, filed Sep. 4, 2003.

Alternatively, the coating is an inorganic composition. Optionally, the coating includes a silicon or silicon oxide moiety. It will be understood by one of skill in the art that the term "silicon oxide" as used herein can be understood to refer to silicon at any level of oxidation. Thus, the term silicon oxide can refer to the chemical structure $SiO_x$, wherein x is between 1 and 2 inclusive. Inorganic coatings for use in the present invention include, but are not limited to, tin oxide, vanadium oxide, manganese oxide, titanium oxide, zirconium oxide, tungsten oxide, and niobium oxide, silicon carbide, silicon nitride, as well as other silicon-containing coatings and/or boron-containing coatings. In some preferred embodiments, the coating comprises a hybrid organic/inorganic composition, such as some embodiments of the silicon oxide cage complexes provided herein. See also the compositions provided in Schubert "Polymers Reinforced by Covalently Bonded Inorganic Clusters" Chem. Mater. 13:3487-3494 (2001); Feher and Walzer "Synthesis and characterization of vanadium-containing silsesquioxanes" Inorg. Chem. 30:1689-1694 (1991); Coronado and Gomez-Garcia "Polyoxometalate-Based Molecular Materials" Chem. Rev. 98:273-296 (1998); Katsoulis "A Survey of Applications of Polyoxometalates" Chem. Rev. 98:359-387 (1998); Muller et al. "Polyoxometalates Very Large Clusters—Nanoscale Magnets" Chem. Rev. 98:239-271 (1998); Rhule et al. "Polyoxometalates in Medicine" Chem. Rev. 98:327-357 (1998); Weinstock "Homogeneous-Phase Electron-Transfer Reactions of Polyoxometalates" Chem. Rev. 98:113-170 (1998); Suzuki "Recent Advanced in the Cross-Coupling Reactions of Organoboron Derivatives with Organic Electrophiles 1995-1998" J. Organomet. Chem. 576:147-168 (1999); Sellier et al. "Crystal structure and charge order below the metal-insulator transition in the vanadium bronze β-$SrV_6O_{15}$" Solid State Sciences 5:591-599 (2003); Bulgakov et al. "Laser ablation synthesis of zinc oxide clusters: a new family of fullerenes?" Chem. Phys. Lett. 320:19-25 (2000); Citeau et al. "A novel cage organotellurate(IV) macrocyclic host encapsulating a bromide anion guest" Chem. Commun., pp. 2006-2007 (2001); Gigant et al. "Synthesis and Molecular Structures of Some New Titanium(IV) Aryloxides" J. Am. Chem. Soc. 123:11623-11637 (2001); Liu et al. "A novel bimetallic cage complex constructed from six $V_4Co$ pentatomic rings: hydrothermal synthesis and crystal structure of $[(2,2'-Py_2NH)_2Co]_3V_8O_{23}$" Chem. Commun., pp. 1636-1637 (2001); and "On the formation and reactivity of multinuclear silsesquioxane metal complexes" 2003 Dissertation Thesis of Rob W. J. M. Hanssen, Eindhoven University of Technology.

In a preferred embodiment, the coating is a silicon-containing coating (e.g., either an inorganic or hybrid inorganic/organic composition) that can be converted to a rigid $SiO_2$ insulating shell after deposition of the coating and association of the nanostructure binding moieties with the surface of the member nanostructure. The present invention provides coated nanostructures in which the second coating comprises a rigid $SiO_2$ shell, and wherein a diameter of the discrete coated nanostructure is optionally less than or equal to 50 nm, less than or equal to 20 nm, less than or equal to 10 nm, less than or equal to 6 nm, or less than or equal to 3.5 nm.

Figure 3:
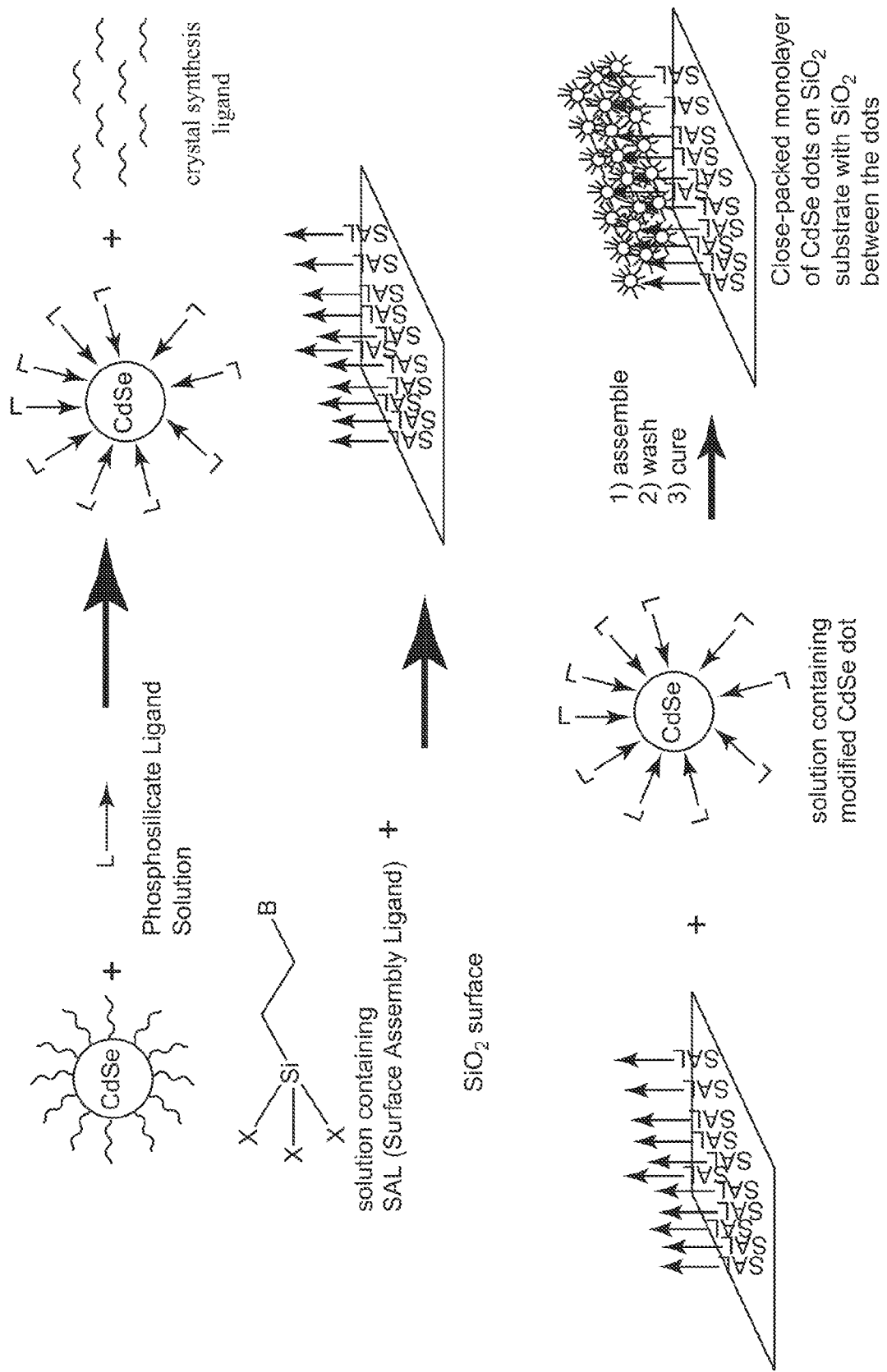
FIG. 3 provides a schematic depiction of the preparation of a substrate using ligand-coated quantum dots. In the top panel, surfactants (crystal synthesis ligands) coating the surface of a CdSe nanodot are exchanged for a phosphosilicate ligand. In the middle panel, an $SiO_2$ surface is coated with a silane ligand to form a self assembled monolayer of surface assembly ligand (SAL). In the bottom panel, the ligand exchanged nanodots are applied to the SAL coated substrate, leaving a close-packed monolayer of CdSe dots on the $SiO_2$ substrate with $SiO_2$ between the dots after assembly, washing, and curing steps.
Figure 4:
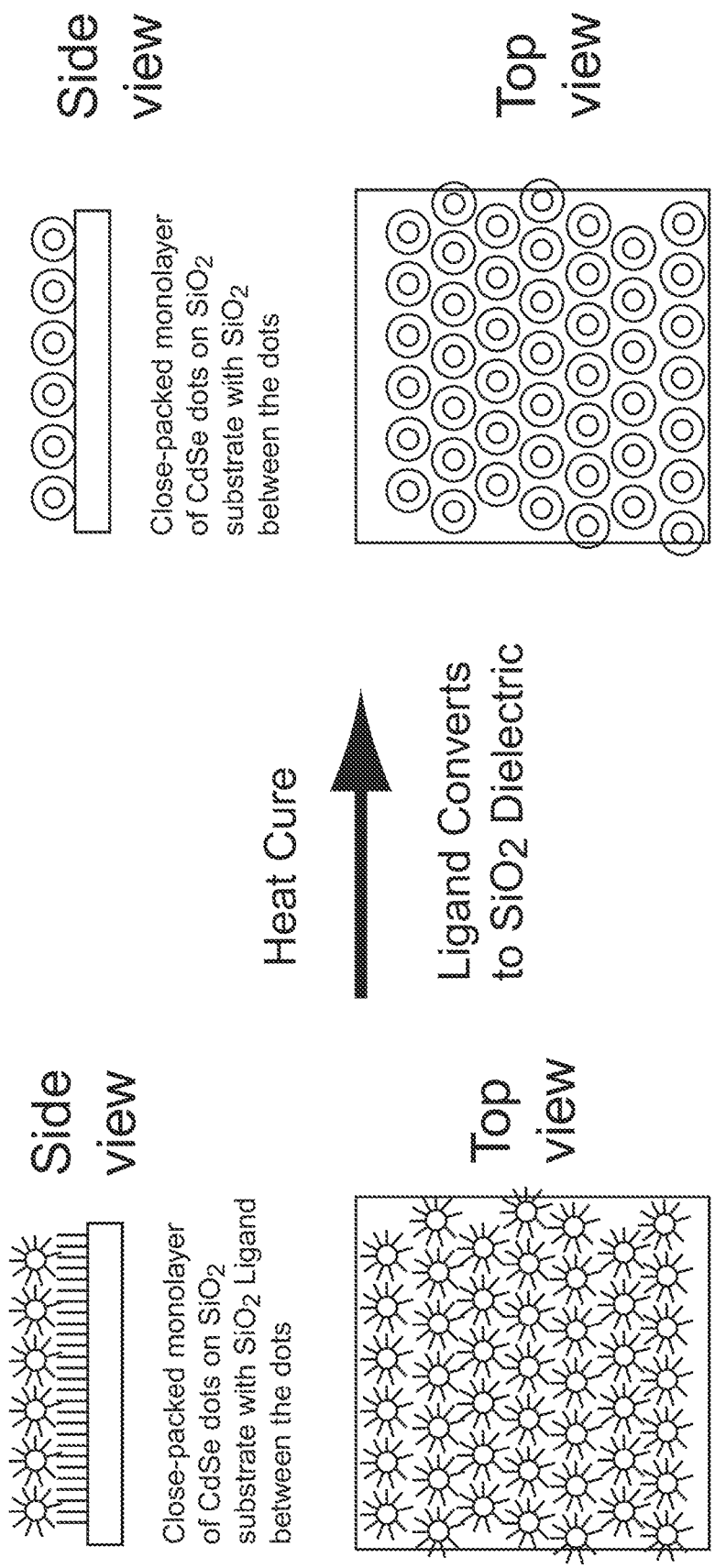
FIG. 4 provides a schematic side-view (top) and top-view (bottom) depiction of the conversion of a first coating to a second coating on a plurality of adjacent quantum dots. The views on the left show a close-packed monolayer of CdSe dots on an $SiO_2$ substrate with an $SiO_2$ ligand between the dots. Following heat curing, during which the ligand converts to an SiO$_2$ dielectric, the views on the right show a close-packed monolayer of CdSe dots on the SiO$_2$ substrate with SiO$_2$ between the dots.

In some embodiments, the coating can be used to provide spacing between adjacent member nanostructures, e.g., during preparation of substrate-bound nanostructure compositions (see, for example, the embodiment depicted in FIGS. 3 and 4). Optionally, the coating ligands of the present invention are sized such that the coated nanostructures can be packed to provide less than about 10 nm between nanostructures (center to center), or optionally less than about 8 nm, less than about 5 nm, or less than about 4 nm between nanostructure centers. In many embodiments, the coating provides a spacing of between about 8-10 nm, about 4-8 nm, or preferably about 2-4 nm between nanostructure surfaces (e.g., the ligands are 1-2 nm in length).

In a preferred embodiment, the coating composition or the rigid shell reduces or prevents charge diffusion between member nanostructures. Coating compositions that can be converted into second coatings of oxides of silicon and/or boron are particularly preferred in this embodiment.

Optionally, after conversion of the ligand coating to a second coating (one that typically has differing properties than the first coating), the coated nanostructures are associated with a substrate and/or overlaid with a topcoat material. Optionally, the top coating material is a similar composition to that of either the first coating or second coating. For example, after formation of rigid $SiO_2$ shells around discrete nanostructures, a plurality of the nanostructures can be overlaid with a composition that can also be converted to $SiO_2$, thus embedding the nanostructures in a matrix of silicon.

The ligands employed as first coatings in the compositions, devices and methods of the present invention are prepared as a means by which to generate a second coating having a selected or desired property (or properties). For example, quantum dots used in flash memory devices need to maintain discrete boundaries between adjacent nanostructures. This can be achieved by providing a ligand that can be converted to a rigid shell (second coating) having a defined diameter, thus controlling the distance between dots. In addition, device performance can be improved if the second coating also functions to improve quantum confinement and reduce cross-talk between quantum dots; a ligand that produces a second coating that has dielectric characteristics is also desirable. The present invention provides ligand compositions for use as first coatings, for use in the generation of discrete coated nanostructures having e.g., improved barrier heights and/or quantum confinement.

The first coating and second coating typically have differing physical properties. For example, the first coating can be electrically neutral (the first electrical property) while the second coating comprises a dipole moment (the second electrical property); similarly, the first coating can comprise a dipole moment while the second coating is electrically neutral. In another embodiment, the first coating is non-insulating or conductive (e.g., a conjugated conducting organic-metal hybrid species), while the second coating is insulating or nonconductive (e.g., a metal oxide). In a further embodiment, the first coating is insulating or nonconductive, and the second coating is non-insulating or conductive. Of particular interest are malleable first coatings that are converted to rigid second coatings (particularly those having semiconductive or insulating properties). One preferred composition embodiment for use as a rigid insulating shell encapsulating the selected nanostructure is silicon oxide ($SiO_2$); such rigid $SiO_2$ second coatings are optionally produced from malleable first coatings comprising silicon oxide caged complexes (e.g., silsesquioxanes).

Alternatively, the first and second coatings may differ in optical properties. For example, the first optical property comprises light absorption or emission at a first wavelength, and the second optical property comprises light absorption or emission at a second wavelength (e.g., by a lanthanide-containing coating or the like). Alternatively, the first optical property could be reduced or non-transmission of light (opaqueness) while the second optical property is transparency (or vice versa). Another embodiment of interest includes first and second coatings that have different bandgap energies, e.g., to alter the electron and/or conductivity properties of the coated nanostructure.

As another example, the first and second coatings can differ in a physical property such as solubility, e.g., in a selected solvent. For example, the first coating can render the coated nanostructures soluble in a selected solvent, to facilitate dispersal, deposition, or the like of the nanostructures, while nanostructures including the second coating are less soluble in the selected solvent. It will be evident that the first and second coatings can have combinations of the above properties; for example, the first coating may increase solubility in a selected solvent, while the second coating is nonconductive.

Silicon Oxide Cage Complexes

Figure 5A:
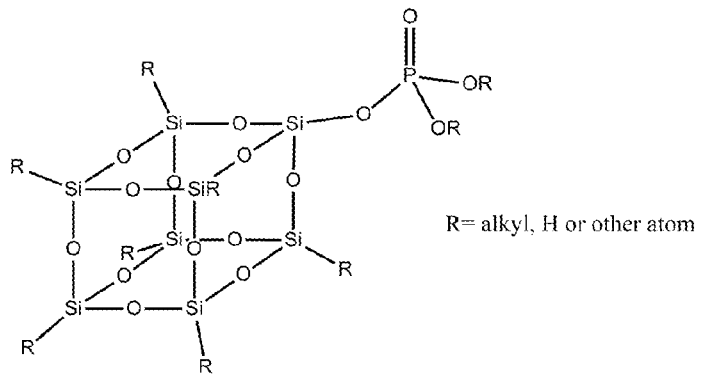
FIGS. 5A-5I provide exemplary first coating compositions of the present invention.
Figure 5B:
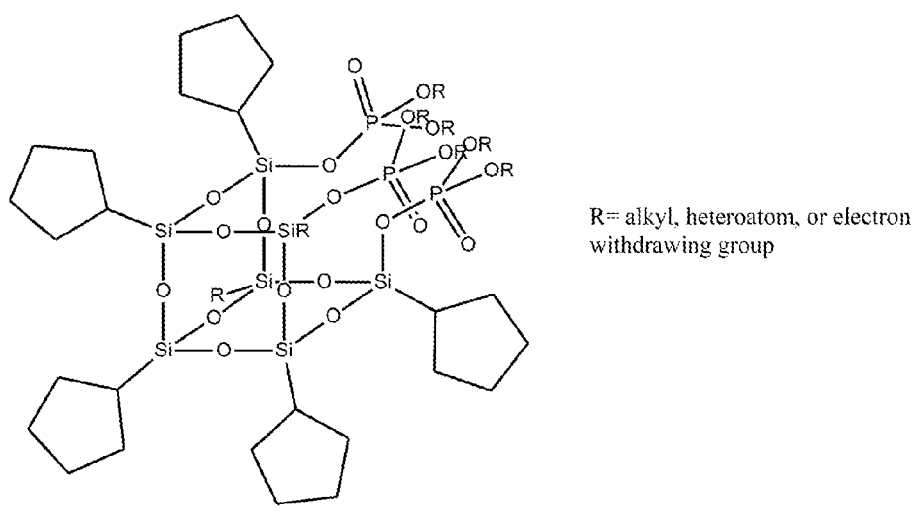
Figure 5C:
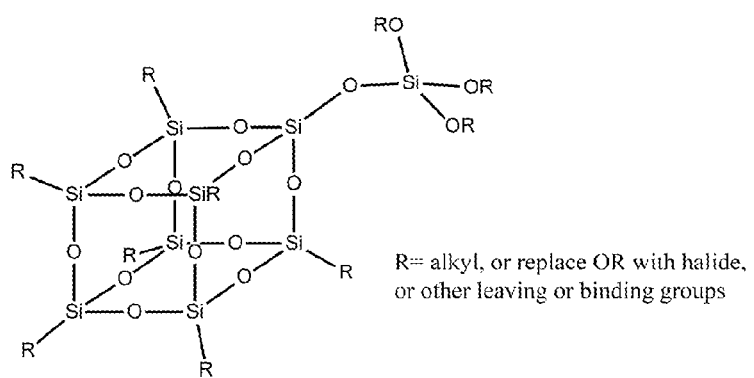
Figure 5D:
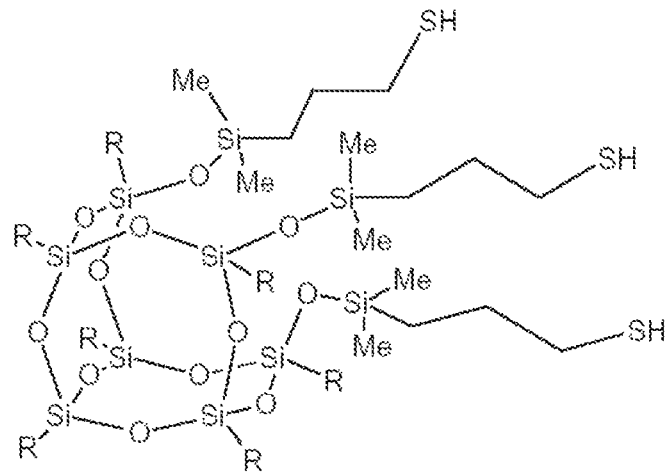
Figure 5E:
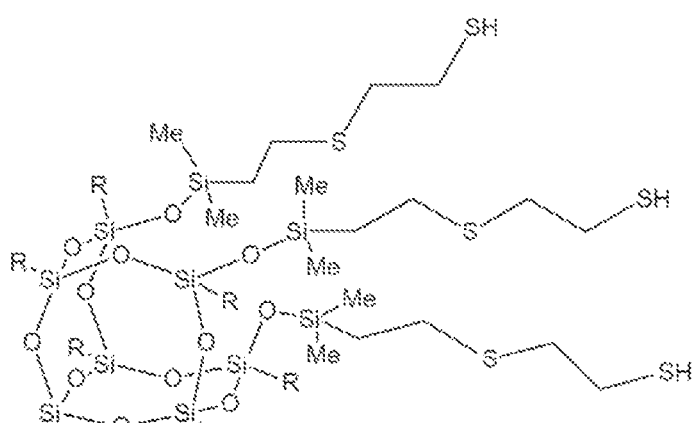
Figure 5F:
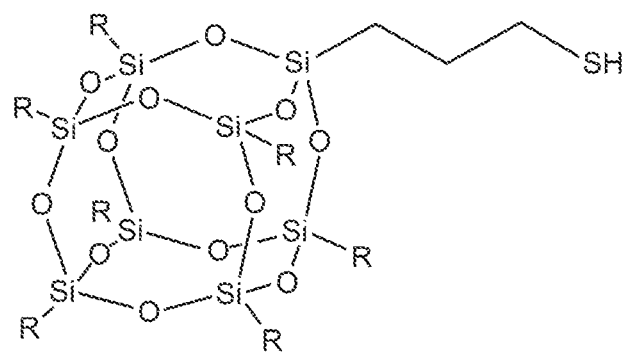
Figure 5G:
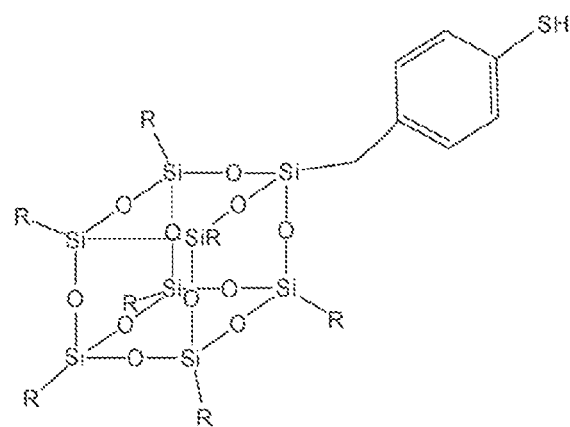
Figure 5H:
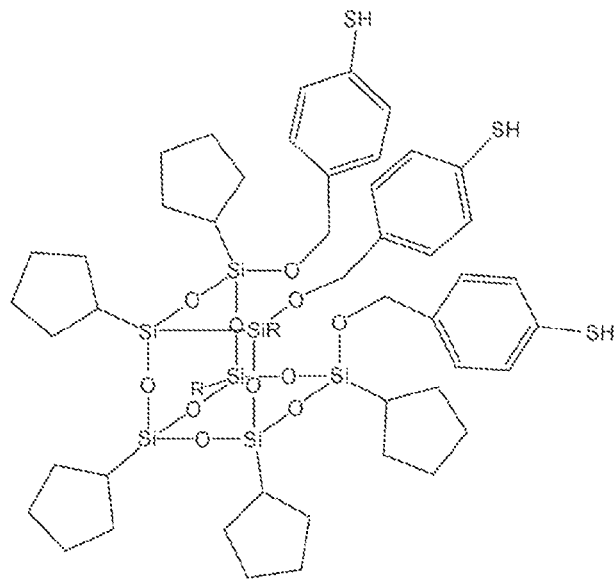
Figure 5I:
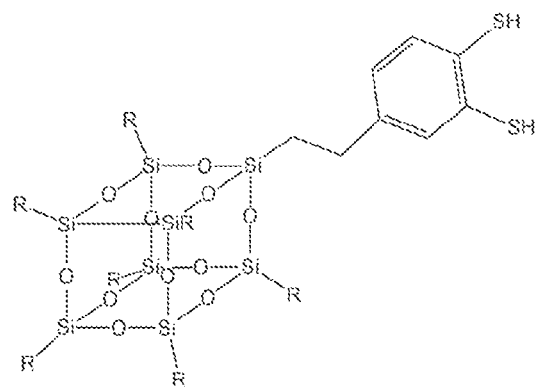

In a preferred embodiment, the ligand coating used to coat the nanostructures is a silicon oxide cage complex. The polycyclic silicon-containing compounds known as silsesquioxanes (or silasesquioxanes), e.g., polyhedral oligomeric silsesquioxanes (POSS), are one type of soluble discrete silicon oxide cage complex (see, for example, Hanssen supra). Exemplary silsesquioxanes include hydrogen silsesquioxane (HSQ) and methyl silsesquioxane (MSQ); additional silsesquioxane structures are provided in FIG. 1 (in which the R groups include a variety of chemical moieties, including, but not limited to, short chain alkyl groups such as methyl, ethyl, isopropyl, isobutyl, longer chain alkyl groups such as isooctyl and norbornyl, as well as aromatic and non-aromatic cyclic structures such as phenyl, cyclopentyl, cyclohexyl and cycloheptyl groups. The silsesquioxane can be either a closed cage structure or a partially open cage structure (e.g., in which some of the ring oxygens are not coupled to both adjacent silicon atoms; see for example, FIG. 5B). The non-silicate organic group, which is located along an edge or at a corner of the cage complex, can be functionalized to accommodate binding of the ligand to an exposed surface of the nanostructure. Optionally, the non-silicate group can function as an electron withdrawing (or electron donating) group. Functional groups which can be incorporated into the silsesquioxane moiety include, but are not limited to, alkyl, alcohol, phosphine, phosphonate, thiol, ether, carboxylate, amine, epoxide, alkene and aryl groups, as well as other nanostructure binding moieties, solubilizing moieties, or electron withdrawing/donating groups of interest.

One preferred derivatization is the incorporation of boron into the silicon oxide cage monomer, which, will produce a second coating of boron oxide and silicon oxide upon heat treatment.

Exemplary silsesquioxane frameworks are provided in FIG. 1. Silsesquioxanes can be either purchased or synthesized, for example, by hydrolytic condensation of $RSiCl_3$ or $RSi(OR)_3$ monomers (see, for example, Feher et al. *J. Am. Chem. Soc.* 111:1741 (1989); Brown et al. *J. Am. Chem. Soc.* 86:1120 (1964); Brown et al. *J. Am. Chem. Soc.* 87:4313-4323 (1965)). The nature of the caged structures formed during synthesis (e.g., type of polyhedral, closed versus open) can be directed by manipulation of the reaction conditions including solvent choice, pH, temperature, and by the choice of R-group substituent (Feher et al. *Polyhedron* 14:3239-3253 (1995)). Additional silsesquioxane frameworks (e.g., for derivatization with nanostructure binding moieties) are available from Hybrid Plastics (Fountain Valley, Calif.; on the world wide web at hybridplastics.com).

Typically, the silsesquioxane frameworks are coupled to one or more nanostructure binding moieties prior to use as compositions or in the methods of the present invention. Any of a number of standard coupling reactions known in the art can be used to derivatize the silsesquioxane framework, e.g., with one or more nanostructure binding head groups. See, for example, the reactions described in Feher et al. *Polyhedron* 14:3239-3253 (1995). Additional information regarding general synthesis techniques (as known to one of skill in the art) can be found in, for example, Fessendon et al. *Organic Chemistry*, 2nd Edition, Willard Grant Press, Boston Mass (1982); Carey et al. *Advanced Organic Chemistry*, 3rd Edition, Parts A and B, Plenum Press, New York (1990); and March *Advanced Organic Chemistry*, 3rd Edition, John Wiley and Sons, New York (1985). Optionally, the standard chemical reactions described therein are modified to enhance reaction efficiency, yield, and/or convenience.

Silsesquioxane compositions for use as first coatings in the present invention include (but are not limited to) the compositions provided in FIGS. 5A-5I and Table 1.

Additional discrete silicates can also be derivatized with nanostructure binding moieties to form compositions of the present invention. For example, cyclopentyltrimethoxysilane (CAS 143487-47-2) will condense with water and assemble into cage structures. The nanostructure binding head group can then be coupled to one or more of the free hydroxyl positions, either before or after cage formation.

Figure 2:
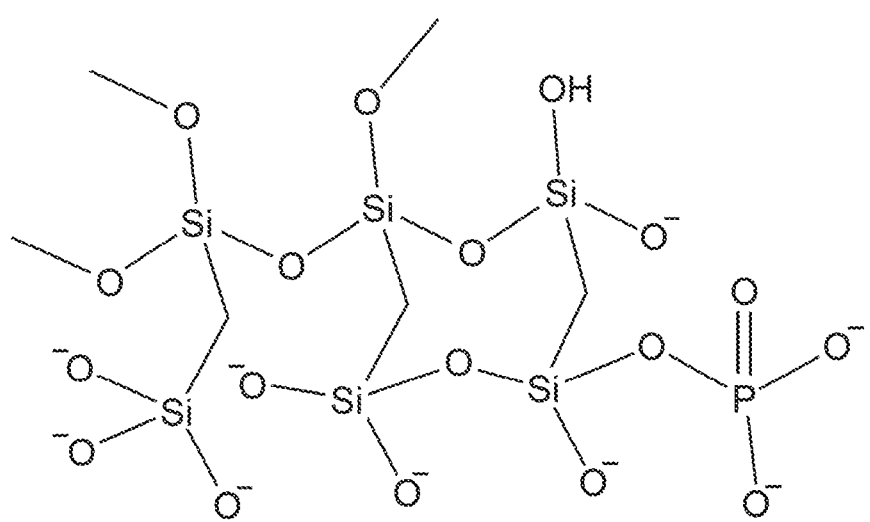
FIG. 2 provides an exemplary discrete silicate ligand having a phosphate moiety incorporated as a nanostructure binding head group.

Phosphosilicate ligands are another preferred embodiment for use in the compositions and methods described herein. As depicted in FIG. 2, the phosphate group on the phosphosilicate ligand can be utilized to couple the ligand to a nanostructure. Preferably, phosphosilicate ligands that could be thermally decomposed into $SiO_2$ are utilized in the methods and compositions of the present invention; shells incorporating $SiO_2$ would lead to higher barrier height than ZnS, and potentially higher temperature tolerances during subsequent processing or manufacturing steps. Exemplary phosphosilicate ligands are provided in FIGS. 5A-5B.

Additional ligands having thiol moieties as the nanostructure binding head groups are depicted in FIGS. 5D-5I. It will be evident that certain nanostructure binding groups are preferred for certain nanostructure compositions; for example, ligands having thiol (e.g., aryl thiol) moieties are preferred ligands for certain metal nanostructures (e.g., Pd nanostructures).

Exemplary nanostructure binding moieties, one or more of which is typically independently coupled to the silicon oxide cage complex via an oxygen or silicon atom, include, but are not limited to: the protonated or deprotonated forms of phosphonate, phosphinate, carboxylate, sulfonate, sulfinate, amine, alcohol, amide, and/or thiol moieties, ester moieties of phosphonate, phosphinate, carboxylate, sulfonate, and sulfinate, phosphines, phosphine oxides, and epoxides.

Polyoxometalates

In other embodiments of the present invention, the ligand coating used to coat the nanostructures is a polyoxometalate. Polyoxometalates are metal-oxygen cluster anions, typically formed from early transition metals (V, N, Ta, Mo and W) in their highest oxidation state. Numerous derivatives can be prepared from polyoxometalate compositions, including halide, alkoxyl, thiol, phospho, and organosilyl derivatives; for a good review, see Gouzerh et al. *Chem. Rev.* 98:77-111 (1990). For example, polyoxovandanate derivatives can be used as first coatings in the compositions and methods of the present invention. The first ligands would then be converted to a second coating comprising vanadium oxide, having properties comparable to those of silicon oxides.

The polyoxometalates can be used as a first coating on the nanostructure, and subsequently converted to a second coating having differing properties. Certain polyoxometalates (for example, acid forms of molybdenum and tungsten-based polyoxometalates) have photochromic or electrochromic properties, which can be reduced or altered upon conversion to a second coating (e.g., by treatment with an organic reducing agent, or by exposure to an externally applied electric field (see, e.g., Yamase *Chem. Rev.* 98:307-325 (1998)).

Other Ligand Compositions

Optionally, the second ligand includes a catechol functional group, which can be used to tune the electrochemical properties of the second coating. Catechol functional groups for use in the present invention include, but are not limited to, pyrocatechol, salicylic acid, and 2,2-biphenol (see, for example, Gigant et al. *J. Am. Chem. Soc.* 123:11632-11637 (2001)).

In many embodiments of the present invention, the second coating is an insulating composition (e.g., used to form an insulating shell around the nanostructure). In a preferred embodiment, the second coating is a metal oxide, or a glass or glass-like composition capable of forming oxide polyhedra. Silicon dioxide ($SiO_2$), boron oxide ($B_2O_3$), and titanium oxide ($TiO_2$) are preferred second coatings components that can be generated from the first coatings of the present invention by, e.g., thermal degradation (although other oxidation states can also be employed). Other second coatings of interest include, but are not limited to, compositions including $GeO_2$, $P_2O_5$, $AsO_5$, $P_2O_3$, $As_2O_3$, $Sb_2O_3$, $V_2O_5$, $Nb_2O_5$, $Ta_2O_5$, $SnO_2$ and $WO_3$, as well as other oxidation states of the provided metal oxides.

Exemplary Compositions

Exemplary compositions for use as the first coating in the present invention are provided in Table 1 below, as well as in FIGS. 5A-5I and 6.

TABLE 1

| Compound 1 | 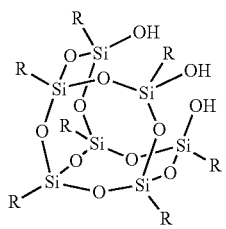 | where R is a cyclopentyl group

| Compound 2 | 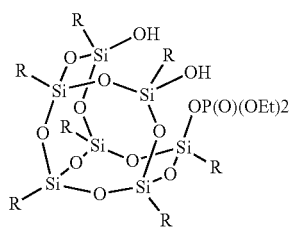 | where R is a cyclopentyl group

| Compound 3 | 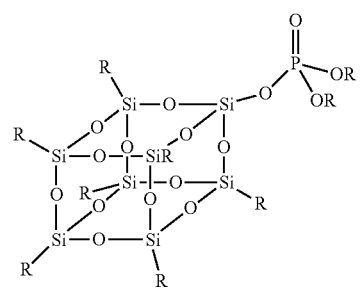 | where R is a hydrogen or alkyl group

| Compound 4 | 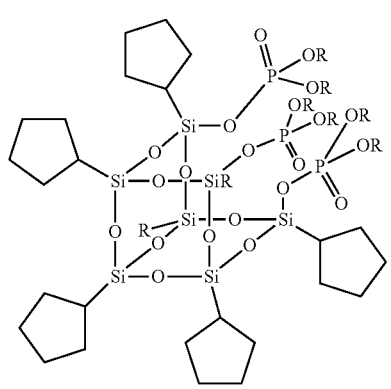 | where R is an alkyl group, a heteroatom, or an electron withdrawing group

TABLE 1-continued

Compound 5

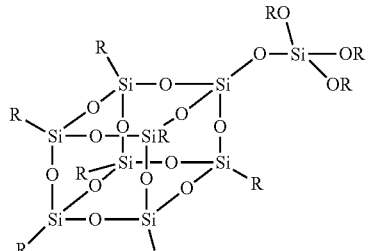

where R is an alkyl group or nanostructure binding group

Compound 6

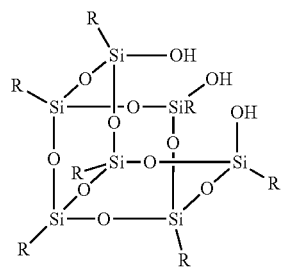

where R is a hydrogen, an alkyl group, or a nanostructure binding group

Compound 7

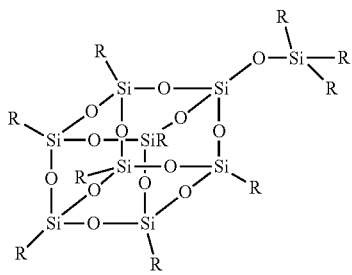

where R is a halide, a leaving group, or a nanostructure binding group

Compound 8

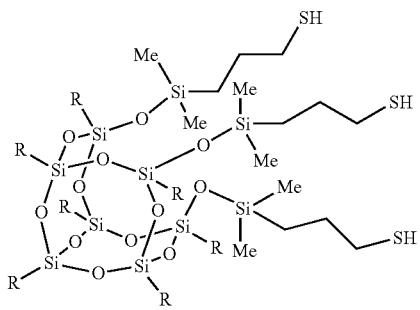

wherein R is an isobutyl group

TABLE 1-continued

Compound 9

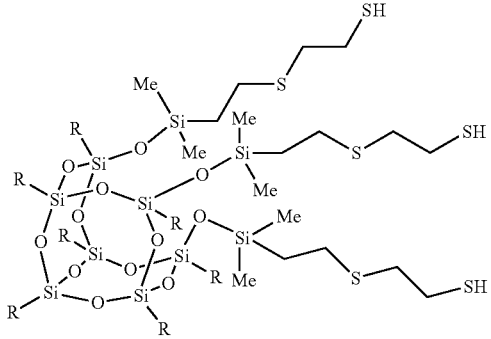

where R is an isobutyl group

Compound 10

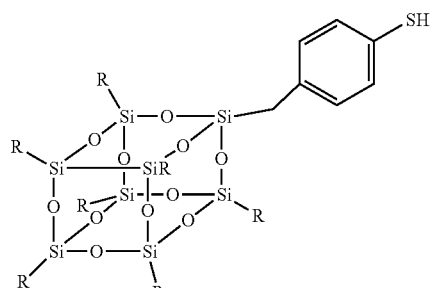

where R is an alkyl group or a hydrogen atom

Compound 11

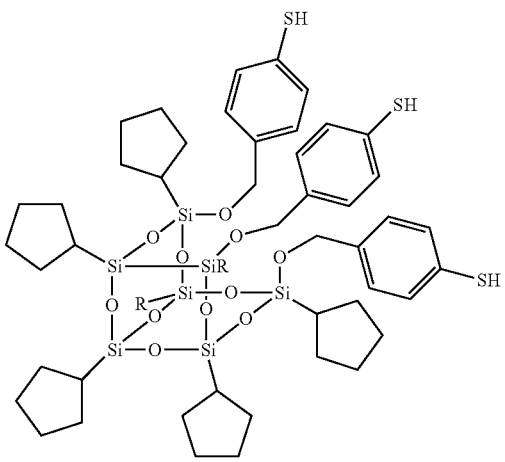

where R is an alkyl group

Compound 12

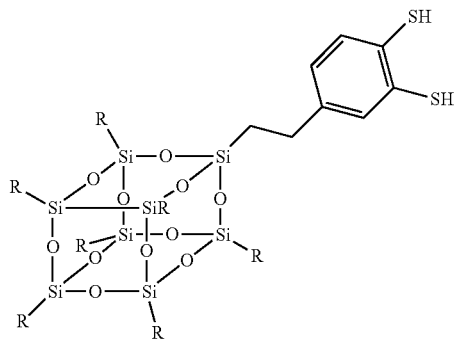

where R is an isobutyl group

TABLE 1-continued

| Compound 13 | 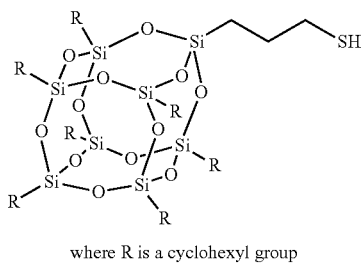 |
|---|---| where R is a cyclohexyl group

Other exemplary compositions for use as the first coating include, but are not limited to, compounds like Compounds 1-3, 5-6, and 8-13, but where R is an organic group or a hydrogen atom. For example, R can be a hydrocarbon group. In certain embodiments, R is an alkyl group (e.g., a cyclic alkyl group or a short alkyl group having fewer than 20 or even fewer than 10 carbon atoms), an aryl group, an alkylaryl group, an alkenyl group, or an alkynyl group. For example, in some embodiments, R is an isobutyl group, a methyl group, a hexyl group, a cyclopentyl group, or a cyclohexyl group.

In one aspect, the present invention also provides compositions for individually coating discrete nanostructures with a dielectric coating. The composition includes a first component comprising a silicon oxide cage complex and a second component comprising one or more nanostructure binding moieties, wherein each nanostructure binding moiety is independently coupled to the silicon oxide cage complex, e.g., via an oxygen or silicon atom. The compositions of the present invention are converted to the dielectric coating after deposition of the composition on a surface of the nanostructure.

Nanostructures

Nanostructures prepared by any of a number of synthetic techniques known in the art can be used to prepare a discrete coated nanostructure of the present invention, including both semiconductor and metallic nanostructures, for example. Typically, the first coating is converted to the second coating after completion of synthesis of the nanostructure, e.g., after the nanostructures have been removed from any solvents or building materials used during the synthesis process. Preferably, the first coating is not difficult to displace from the nanostructure surface.

Optionally, the nanostructures are associated with the surface of a substrate, such as a silicon wafer or a TEM grid. In some embodiments, the substrate has been treated with a composition for association with the nanostructures, such as a functionalized self-assembly monolayer (SAM) ligand. Exemplary compositions for functionalizing the substrate surface include a silicon nitride coating, a silane ligand having a nanostructure binding moiety, or other chemical moiety that can provide or accept a proton for hydrogen-bonding to the coated nanostructure (e.g., amine, alcohol, phosphonate, fluorine or other non-carbon heteroatom). For example, the silane ligand can include structures having the formula [$X_3$Si-spacer-binding group(s)] where X is a Cl, OR, alkyl, aryl, other hydrocarbon, heteroatom, or a combination of these groups, and where the spacer is an alkyl, aryl and/or heteroatom combination. Optionally, the structure of the ligand can be responsive to light activation, leading to crosslinking of ligands (e.g., to each other, or the surface of the SAL coated substrate) via inclusion of a photo-crosslinkable group. Exemplary surface ligands for use in the present invention (referred to generically as "SAL" in FIG. 4) are commercially available from Gelest Inc. (Tullytown, Pa.; on the world wide web at gelest.com).

The individual nanostructures employed in the compositions include, but are not limited to, a nanocrystal, a nanodot, a nanowire, a nanorod, a nanotube, a quantum dot, a nanoparticle, a nanotetrapod, a tripod, a bipod, a branched nanocrystal, or a branched tetrapod. The present invention is not limited to either semiconductor nanostructures or metallic nanostructures; the type of nanostructure employed is determined in part by the purpose for which it is intended. While any of these nanostructure embodiments can be used in the present invention, spherical, nearly spherical, and/or isotropic nanocrystals such as nanodots and/or quantum dots are used as the prototypical nanostructure for illustration purposes. For many embodiments, the diameter (e.g., a first dimension) of the coated nanodot or quantum dot is less than about 10 nm, and optionally less than about 8 nm, 6 nm, 5 nm, or 4 nm. In some embodiments, the nanostructure (e.g., dot) diameters ranges from about 2 nm to about 4 nm. In a preferred embodiment for use with densely-packed nanostructure arrays, the diameter of the coated quantum dot or nanodot is less than or equal to about 6 nm, or optionally less than or equal to about 3.5 nm.

Nanostructures, such as nanocrystals, quantum dots, nanoparticles and the like, can be fabricated by a number of mechanisms known to one of skill in the art. Furthermore, their size can be controlled by any of a number of convenient methods that can be adapted to different materials, and they are optionally washed to remove excess surfactants remaining from their synthesis and/or excess ligands. See, e.g., Scher et al. U.S. patent application Ser. No. 10/796,832, filed Mar. 10, 2004; Scher et al. U.S. Provisional Patent Application Ser. No. 60/544,285, filed Feb. 11, 2004; Scher et al. U.S. Provisional Patent Application Ser. No. 60/628,455, filed Nov. 15, 2004; and Whiteford et al. U.S. Provisional Patent Application Ser. No. 60/637,409, filed Dec. 16, 2004; and references therein.

The nanostructures employed in the nanostructure-containing compositions of the present invention can be fabricated from essentially any convenient materials. For example, the nanocrystals can comprise inorganic materials, e.g., a semiconducting material selected from a variety of Group II-VI, Group III-V, or Group IV semiconductors, and including, e.g., a material comprising a first element selected from Group II of the periodic table and a second element selected from Group VI (e.g., ZnS, ZnO, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and like materials); a material comprising a first element selected from Group III and a second element selected from Group V (e.g., GaN, GaP, GaAs, GaSb, InN, InP, InAs, InSb, and like materials); a material comprising a Group IV element (Ge, Si, and like materials); a material such as PbS, PbSe, PbTe, AlS, AlP, and AlSb; or an alloy or a mixture thereof. Metals such as Pd, Pt, Au, Ag, Ni, Fe, Sn, Zn, Ti, Ir, and Co can also be used in the synthesis of nanostructures for use in the present invention, as can metal oxides. Further details regarding nanocrystalline structures for use in the present invention can be found, for example, U.S. patent application Ser. No. 10/656,802, filed Sep. 4, 2003, incorporated herein by reference in its entirety for all purposes.

In a preferred embodiment, the devices of the present invention employ nanostructures comprising small, roughly spherical CdSe or Pd nanocrystals, or other metal or semiconductor-based nanostructures that can be synthesized as spherical, nearly spherical, and/or isotropic nanoparticles (such as nanodots and/or quantum dots).

Methods for Post-Deposition Shell Formation on a Nanostructure

Methods for making and using core/shell CdSe/ZnS semiconductors prepared via deposition on or in a layer of conducting organic material are known in the art, but these methods present several problems. For example, the thin ZnS shell of the nanostructure:shell construct does not have a high enough energy barrier to prevent leakage of the charge from of the nanostructure. While this problem can be addressed by growing a very thick ZnS shell, this approach is synthetically impractical, as after several monolayers, the strain causes defect formation, the nanocrystals become insoluble, and the spacing between the nanocrystals would be too large to meet the packing density desired for memory applications. The problem could theoretically be addressed by growing a core structure (CdSe) having a first shell (ZnS) and an additional shell ($SiO_2$), however, this approach would also have the same disadvantages with respect to defect formation, solubility and spacing. The present invention circumvents these problems, either by performing a ligand exchange directly onto the selected nanostructure using a ligand that can be turned into a second coating (for example, an oxide) upon curing but will maintain the nanostructure solubility in organic solvents (e.g., for deposition purposes), or by growing the nanostructures in the presence of such a ligand.

The present invention provides methods for post-deposition shell formation on a nanostructure. These methods include the steps of a) providing one or more nanostructures having a ligand composition associated with a first surface, which a ligand composition is capable of being converted to a second coating having differing electrical, optical, physical or structural properties (e.g., to a rigid shell), and b) curing the ligand composition and generating the second coating (e.g., the rigid shell) on the first surface of the nanostructure, thereby forming a shell on the nanostructure post-deposition of the ligand composition on the nanostructure. The methods of the present invention are preferably performed at temperatures that do not compromise or degrade the structural and/or physical properties of the nanostructure.

In one class of embodiments, the nanostructures having the ligand composition associated therewith are provided by exchanging surface ligands. In this class of embodiments, providing one or more nanostructures having a ligand composition associated with a first surface comprises providing one or more nanostructures having one or more surfactants associated with the first surface and exchanging the surfactants on the first surface with the ligand composition. In another class of embodiments, the nanostructures are synthesized in the presence of the ligand composition, and no ligand exchange is necessary.

Providing the Nanostructures

The methods of the present invention can be used to generate a shell or second coating on any of a number of nanostructures, including, but not limited to, a nanocrystal, a nanodot, a nanowire, a nanorod, a nanotube, a quantum dot, a nanoparticle, a nanotetrapod, a nanotripod, a nanobipod, a branched nanostructure, and the like. Furthermore, the methods of the present invention are not limited to nanostructures prepared by a specific synthetic approach. For example, organometallic solution-based syntheses of Pd, CdSe, CdTe and CdS nanocrystals typically employ various surfactants and/or fatty acids as solubilizing agents (see, e.g., Peng et al. U.S. Patent Publication No. 2002/0066401, Peng et al. U.S. Patent Publication No. 2003/173541, Kim et al. *NanoLetters* 3:1289-1291 (2003), and Qu et al. *NanoLetters* 1:333-337 (2001), and references cited therein). Nanostructures prepared using these or other weakly-binding organic compositions can be employed in the methods of the present invention.

Exchanging Surface Ligands

In some embodiments of the methods, the nanostructures are provided by preparing or growing the initial structures (e.g., the core nanostructure components) in the presence of a weakly binding organic composition (the "growth ligand"). The growth ligand has a weaker association with the nanostructure than the ligand used to generate the first coating (a "replacement ligand"), and thus can be readily exchanged, e.g., by mass action.

The nanostructures employed in the methods of the present invention commonly have one or more organic compositions, or growth ligands, associated with the nanostructure surface (e.g., for solubilizing the nanostructure during the synthesis procedure). Typical growth ligands include surfactants, for example, phosphines or phosphine oxides such as trioctyl phosphine (TOP), tri-n-butyl phosphine (TBP), or trioctyl phosphine oxide (TOPO) or acids such as hexadecyl phosphonic acid (HDPA) or octadecyl phosphonic acid (ODPA). Alternatively or in addition, various long chain carboxylic acids (e.g., fatty acids, such as stearic, palmitic, myristic, lauric, capric, caprylic, caproic and butyric acids, as well as other saturated or nonsaturated lipid-like structures) may have been employed during synthesis and remain associated with the nanostructure surface. In the methods of the present invention, the growth ligands are exchanged for a ligand composition capable of being converted to a second ligand or second coating having a different electrical, optical, physical or structural property, thereby forming a ligand-exchanged nanostructure composition. In a preferred embodiment, the growth ligands are exchanged for a ligand composition capable of being converted to a rigid insulating shell, such as an oxide.

Exchanging the surfactants associated with the nanostructure surface with a ligand or first coating of the present invention can be achieved by any of a number of mechanisms known in the art. In one embodiment, exchanging the surfactants involves suspending or dissolving the nanostructures in an organic solvent, and combining the suspended nanostructures with the ligand composition. Solvents that can be used for the exchange process include any that are typically employed in conjunction with nanostructure synthesis and processing, such as toluene, chloroform, chlorobenzene, and the like. The temperature at which the exchanging step is performed will depend upon the ligands involved and may range from room temperature to elevated temperatures equal or greater than 100° C., 200° C., 300° C. and the like. For example, surface ligands comprising sulfonic acid moieties can be exchanged without substantial heating, and optionally can be performed at room temperature.

In another embodiment, the nanostructures are coupled to or associated with a substrate surface (e.g., a solid phase embodiment rather than in solution). The organic surfactants on the nanostructure surface can be removed in situ, for example, via a low temperature organic stripping process (at temperatures<500° C., and optionally between 200-350° C.). The stripping process is optionally followed by oxidation using, e.g., a reactive oxygen species. The replacement ligand (e.g., the ligand of the first coating) is subsequently applied to the nanostructure by any of a number of techniques known in the art (vapor deposition, spraying, dipping, etc.).

Self Assembly of Monolayers

Optionally, the ligand coated nanostructures are induced to form monolayers due to intermolecular self-assembly forces. For example, in a preferred embodiment, the present invention provides nanocrystals with silsesquioxane or silicate ligands tailored for charge storage applications. Preferably, the nanostructures are arranged into close packed arrays, or more preferably high density and/or ordered close-packed arrays. Controlled self-assembly of the close-packed arrays can be achieved by various wet-process methods, such as deposition of the nanostructure-first ligand composition onto self-assembled monolayers (SAMs) or otherwise functionalized substrates or oxides, or by evaporation-driven assembly.

The member components of the self-assembled monolayer associate with both the surface of the substrate as well as the nanostructure, thus forming a bridge or linker between the two. Various SAM compositions for use in the present invention include, but are not limited to, organosilanes, phosphonic acids, phosphines, thiols, amines, heteroatoms, and the like. In one preferred embodiment, the SAM consists of a silane ligand with a binding head for the silsesquioxane or silicate ligand. In an alternate preferred embodiment, the substrates are directly functionalized with binding groups suitable for binding to the nanocrystals. The nanostructures are applied in a solution and deposited on the SAM or functionalized substrate by, e.g., spin-coating, dip-coating, spray-coating, or conventional printing technologies. The excess (unbound) nanostructures are subsequently washed off the substrate using an organic solvent such as toluene or chloroform, resulting in a monolayer of nanocrystals coated with silicon-containing ligands.

Alternatively, the monolayers can be prepared by evaporation-driven assembly, without the need of specially treated substrates. The nanocrystals are deposited on the substrate from solution by spin-coating, dip-coating, spray-coating, or conventional printing technologies. By controlling the de-wetting process of the solvent, well-ordered arrays of nanocrystals can be obtained.

Further details regarding monolayer formation can be found, for example, in Heald et al. U.S. Provisional Patent Application Ser. No. 60/671,134, filed Apr. 3, 2005, incorporated herein by reference in its entirety for all purposes.

Curing the Ligand Composition and Generating the Second Coating

After deposition and monolayer formation, the substrate can be thermally annealed to cure the layer of first coating (and thereby form the second layer, which in some embodiments is a rigid insulating shell, on the first surface of the nanostructure). The technique used for the curing step will depend upon the type of ligand composition employed in the method. The curing can be done under inert atmosphere, such as argon or nitrogen, or under oxygen, for example. The temperature of the curing process can be adjusted for the surface ligands. For example, curing the composition can involve heating the nanostructure having the ligand composition associated therewith to form the rigid shell on the nanostructure surface. Heating can be performed in one or more stages, and using various equipment such as a hot plate or quartz furnace (see Yang et al. *Proc. Natl. Acad. Sci.* 25:339-343 (2001)). In some embodiments, the ligand:nanostructure complex is heated to less than about 500° C., and optionally, to between 200-350° C. Thermal curing of silsesquioxane ligands typically involves heating the silsesquioxane-containing composition to temperatures of less than about 500° C., and preferably less than about 350° C., thereby transforming the cage structures into a network structure. In other embodiments involving silicon-containing ligands, the thermal curing process decomposes the first coating into a second coating of $SiO_2$. Conversion of the first coating to the second coating (or shell) can be monitored, for example, via thermogravimetric analysis using an FTIR spectrometer (see Yang (2001) supra, and references cited therein).

In alternate embodiments, conversion of the ligand composition from the first coating to a second coating or shell having altered electronic or optical properties can include irradiating the composition. For example, for embodiments employing PMMA precursors or carboxylate diene or diacetylene moieties, the polymerization process is light activated, leading to crosslinkage of the first coating to form the organic shell (second coating).

In some embodiments, the one or more nanostructures provided in the methods of the present invention are coupled to a substrate via a second nanostructure surface. Optionally, this substrate is a silicon wafer. In some embodiments, the member nanostructures are encapsulated prior to association with the substrate surface, while in other embodiments, a first portion of a member nanostructure is associated with the substrate, and a second portion of the member nanostructure is associated with the first coating or the second coating. Optionally, the surface of the silicon wafer includes a silane ligand coupled to a second nanostructure binding moiety, e.g., to facilitate association of the substrate with a portion of the nanostructure surface.

The curing process is optionally followed by spin coating of another layer of e.g., first coating, silicate, or the like, onto the substrate-bound coated nanostructures, and thermal curing, thereby providing a top coating or overlay. In some embodiments, the top layer is an insulating oxide layer. The methods of the present invention optionally further include the step of applying a planarization composition as the overlay or top coating composition applied to the substrate-coupled nanostructures. The optional planarization composition can be applied either before or after the step of curing the ligand composition. The planarization composition fills any remaining narrow spaces and produces a (relatively) flat surface on the treated portion of the wafer and/or nanostructure composition. Preferably, the top coating or planarization material is compatible with the rigid shell of the coated nanostructure. Optionally, the planarization composition is a dielectric material (either similar or different in composition from the second coating composition).

Exemplary planarization materials include, but are not limited to, various silicates, phosphosilicates, and siloxanes referred to as Spin On Glass (SOG). Optionally, the ligand compositions of the present invention can be used as the planarization composition.

The present invention also provides nanostructures having a rigid shell formed post-deposition as prepared by the methods described herein. In a preferred embodiment, the rigid shell comprises silicon or silicon oxide, and the diameter of the nanostructure:shell composition is less than or equal to about 6 nm.

Compositions for Modulating Nanostructure Energy Levels

In one aspect, the present invention is directed toward methods and ligand compositions for manipulating the electronic properties of nanostructure compositions. The ligand-associated nanostructure compositions are preferably employed in the absence of a polymeric matrix, thereby removing a factor that might interfere electronically with the nanostructure, as well as minimizing the organics present in the device. The compositions can be readily incorporated into the manufacturing process of various nanostructure-containing devices, such as those described in Scher et al. U.S. patent application Ser. No. 10/778,009, filed Feb. 11, 2004.

Thus, in one aspect the methods of the invention employ various ligand compositions to alter the energy state of a nanostructure composition. In preferred embodiments, the ligand compositions of the invention include a body structure containing a dipole moiety, and a nanostructure binding moiety coupled to the body structure.

A dipole in essence is a non-uniform charge distribution across a molecule. While dipoles are typically portrayed as a pair of equal and opposite charges within the molecule, the dipole may also arise due to the presence of magnetic poles rather than electric charges (e.g., a defined charge is not necessarily required for the molecule to have a dipole moment). The dipole can be permanent (e.g., due to substantially different electronegativities of constituent atoms) or inducible (e.g., in which the separation of charge occurs, for example, due to exposure to an external factor, such as light).

The process of associating a ligand composition of the invention with a target nanostructure alters the energy levels of the nanostructure, thereby adjusting the electron donor/acceptor ability of the composition. The Fermi level of a solid is the energy level at which the Fermi-Dirac distribution function is equal to 0.5 (e.g., midway between the highest occupied molecular orbital and the lowest unoccupied molecular orbital). Association of two materials (e.g., a nanostructure and a ligand composition) having two differing Fermi levels will result in a contact potential and electron flow as the Fermi levels equilibrate. Thus, it would be highly advantageous to be able to manipulate the relative Fermi levels of the components in a nanostructure composition; how well the energy levels of components in a device align or match are important considerations during the process of component selection and device fabrication.

Energy levels of nanoscale components are different from the energy levels of their non-nanoscale (bulk) counterparts. These differences are due, at least in part, to quantum confinement effects. As provided herein, modulation of the energy levels of nanostructure compositions (beyond that due to quantum confinement effects) is possible by modification of the nanostructure surface using, e.g., the ligand compositions of the invention. Specifically, introduction of dipoles on the nanostructure surface affects the energy levels of the nanostructure. While the invention is not limited to a particular theory, the presence of the charge distribution provided by the dipole is thought to assist in the transport of electrons and/or holes in a manner similar to that described for the use of a forward bias current. In addition, the use of electroactive ligands such as the dipole ligands provided herein optionally improves the solubility, and hence the morphology, of the nanostructure composition; upon appropriate alignment of the energy levels of the ligand, the transportation and/or extraction of charges is not diminished or otherwise affected.

Further energy level adjustment of the dipole ligand with respect to the nanostructure can be accomplished by the addition of electron-donating or electron-withdrawing characteristics to the ligand (either as part of the dipole, or in addition to the dipole). Incorporation of electron donor-type dipole ligands would likely increase the energy level of the highest occupied molecular orbital (HOMO) of the ligated nanostructure composition as compared to the nanostructure sans ligand. Conversely, utilization of ligands having electron-withdrawing constituents (e.g., electron acceptors) would potentially decrease the HOMO level. Through selection of dipole and supplementation of the ligand with electron-donating or electron-withdrawing moieties, the energy levels of a given nanostructure composition can be deliberately modulated and/or matched according to the desired band level alignment of a given device.

Various aspects of the dipole ligand can be altered, depending upon the desired effect upon the nanostructure energy level. For example, the magnitude of the dipole can be adjusted, as can the number of dipoles present within a given ligand (e.g., the multiplicity). A selected ligand composition can be further modified or supplemented with additional chemical constituents, e.g., to manipulate other physical parameters, such as solubility characteristics of the ligand composition. Furthermore, different nanostructure binding moieties can be employed, based upon the composition of the nanostructure to be bound.

Nonconjugated Ligand Compositions

In some embodiments, the invention provides ligand compositions having a nonconjugated body structure containing a dipole moiety, as well as a nanostructure binding moiety coupled to the nonconjugated body structure at a first position. While the elements of the dipole may be conjugated (e.g., to facilitate charge separation), the core of the body structure is not conjugated in these embodiments (e.g., charge is not transferred through or across the body structure).

An exemplary type of nonconjugated body structure for use in the ligand compositions of the invention are carborane compositions. Carboranes are typically icosahedral structures composed of carbon, boron and hydrogen (e.g., $C_2B_{10}H_{12}$). The structures are remarkably stable to both thermal and chemical conditions; however, they can be modified at either the mildly acidic C—H vertices or at the less reactive B-H positions (see, e.g., Jiang et al. *Inorg. Chem.* 34:3491-3498 (1995); and Zheng et al. *Inorg. Chem.* 34:2095-2100 (1995)).

Optionally, the carborane-type ligand compositions of the invention include one or more additional substitutions. Exemplary chemical moieties for coupling to the carborane body structure include, but are not limited to, various heteroatoms, alkyl moieties, alkenyl moieties, alkynyl moieties, and aromatic groups. Optionally, a combination of additional substituents can be employed in the ligand composition.

Carborane ligands for use in the present invention can be prepared using conventional chemistries, such as those provided in Li et al. (1991) *Inorg. Chem.* 30:4866-4868; Zheng et al. (1995) *Inorg. Chem.* 34:2095-2100; Marshall et al. *Organometallics* 20:523-533 (2001); Fox et al. *J. Material Chem.* 12:1301-1306 (2002); and Lee et al. *Chem Comm.* 2485-2486 (2000).

Exemplary carborane-type ligand compositions include, but are not limited to, the compounds provided in Table 2. The darkened vertices denote the position of carbon atoms within the structure.

TABLE 2

Compound 14

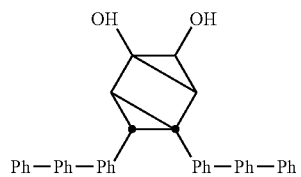

TABLE 2-continued

Compound 15

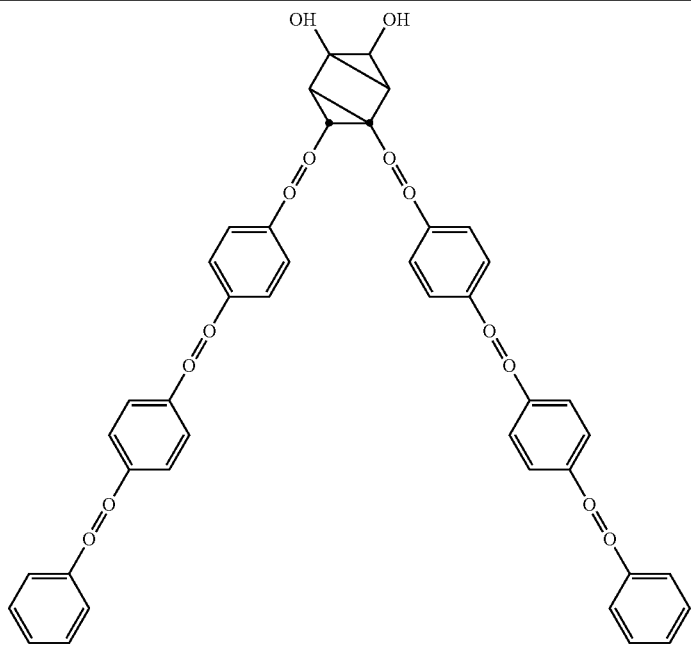

Other boron-containing compositions can also be employed as the nonconjugated body structure in the ligand compositions. For example, boron derivatives (e.g., boronic acids) of polyhedral oligomeric silsesquioxanes (POSS), including the silsesquioxanes described above and in U.S. Provisional Patent Application Ser. No. 60/578,236, filed Jun. 8, 2004 can be employed as ligand compositions. These ligand compositions can be prepared, for example, by functionalizing the free hydroxyl groups of the silsesquioxane or other silicon oxide cage complex using a Lewis acid boron, e.g., $B(OR)_3$, where each R is (independently) an alkyl moiety or a hydrogen.

In an alternate embodiment, the nonconjugated body structure for use in the ligand compositions of the invention is a fluorine-containing composition. In some embodiments, the fluorine containing composition includes a silicon monofluoride (SiF) or a SiF derivative. In other embodiments, the ligand composition is trifluoroacetic acid (in which the carboxyl group functions as the nanostructure binding moiety).

In a further embodiment of the invention, the ligand composition includes a nanostructure binding moiety coupled to a light-activated intramolecular salt. One embodiment of this type of ligand is $H_2O_3PCH_2CH_2CH(NH_3^+)CH_2COO^-$.

Conjugated Ligand Compositions

In a further aspect, the invention provides various dipole-containing ligand compositions that contain a conjugated body structure. For example, the invention provides ligand compositions for modulating nanostructure energy levels having a body structure comprising a light-activated spiropyran salt, and a nanostructure binding moiety coupled to the body structure (e.g., at a first position). Spiropyrans are photochromic materials that can be converted from a conjugated spirobenzopyran ring structure to an (often colored) merocyanine open-ringed structure.

In another embodiment, the invention provides ligand compositions for modulating nanostructure energy levels having a body structure comprising a boron-containing oligomer, and a nanostructure binding moiety coupled to the body structure (e.g., at a first position). Optionally, the boron-containing oligomer is a composition having the formula $(A-B)_n$, where A is an aryl moiety, and B is a boron atom. In these compositions in which the boron atom alternates with the aryl group, the boron atoms are preferably positioned para, or optionally meta, to one another (e.g., they are not adjacent to one another on an aromatic ring structure). Exemplary aryl moieties for use in the boron oligomeric compositions include, but are not limited to, a benzene, a thiophene, a phenylene, an aniline, and a pyridine.

An exemplary ligand composition includes, but is not limited to, the compound provided in Table 3.

TABLE 3

Compound 16

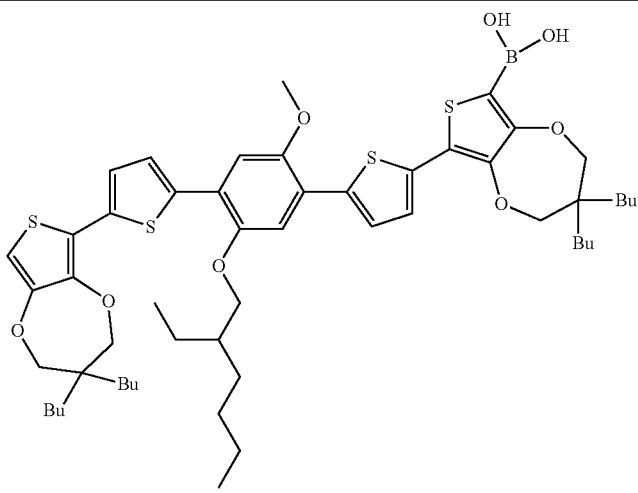

In one embodiment, the ligand composition includes a body structure comprising a thiophene moiety and a nanostructure binding moiety coupled to the body structure at a first position. The body structure optionally comprises a dipole, and the body structure optionally includes two, three, four, or even more thiophene moieties. The ligand optionally comprises a boron atom, e.g., within the nanostructure binding moiety. For example, the nanostructure binding moiety can be a boronic acid group, as in exemplary compound 16.

In addition to the ligand structures provided herein, additional conjugated organic body structures which can be derivatized with dipole elements can be found, e.g., in PCT Publication No. WO2004/022714 and related Whiteford et al. U.S. patent application Ser. No. 10/656,910 and Whiteford et al. U.S. patent application Ser. No. 10/928,625.

Nanostructure Binding Moieties

The energy level modulating ligand compositions of the invention are most effective when physically coupled to the surface of the nanostructure. Attachment can be achieved via a nanostructure binding moiety, e.g., a chemical constituent either naturally part of or added to a selected body structure, which chemical constituent can interact with and bind to or otherwise associate with the nanostructure. Exemplary chemical moieties for use as a nanostructure binding moiety in the methods and compositions of the invention include, but are not limited to, phosphonic acid, phosphinic acid, carboxylic acid, hydroxyl, amine, amine oxide, phosphine, phosphine oxide, phosphonate, phosphonite, carbamate, urea, pyridine, isocyanate, amide, nitro, pyrimidine, imidazole, salen, dithiolene, catechol, N,O-chelate ligand, P,N-chelate ligand, and thiol moieties (or combinations thereof). Alternatively, nitrogen-containing aromatic compounds or heterocycles (e.g., imidazoles, benzoimidazoles, pyridines, pyrimidines, purines, or quinolines) can also be used as nanostructure-binding head group moieties in the compositions of the invention. Additional exemplary nanostructure binding groups have been noted above. (Similarly, any of these nanostructure binding groups can be employed in the other ligands described herein.) Exemplary compounds include, but are not limited to, derivatives of 2-methylpyridine, 3-ethylpyridine, 4-chloropyridine, collidine, dimethylquinoline, and other compounds commonly used as nanostructure growth terminators (see, e.g., Alivisatos et al. U.S. Pat. No. 6,306,736). Optionally, a ligand composition can bear two or more nanostructure binding moieties. Additional information regarding functional groups for associating ligands to nanostructures is provided, e.g., in Whiteford et al. PCT Publication No. WO2004/022714.

Furthermore, a second dipole can optionally be coupled to any of the ligand compositions provided herein. Typically, this second dipole is coupled, e.g., to the nonconjugated or conjugated body structure, at a second position relative to the first position (at which the nanostructure binding moiety is attached).

The present invention also provides nonpolymeric nanostructure compositions having a plurality of nanostructures, wherein each member nanostructure is coupled to a plurality of a selected ligand composition.

Methods for Modulating Nanostructure Energy Levels

In addition to various ligand compositions, the invention also provides methods for modulating an energy level of a nanostructure in the absence of a polymeric matrix. The methods of the invention include the steps of a) providing a nanostructure having a first energy level; b) selecting a ligand composition comprising a dipole, wherein the ligand composition has a second energy level as compared to the first energy level of the nanostructure; and, c) associating or coupling the ligand composition to a surface of the nanostructure, thereby modulating the energy level of the nanostructure.

The "band theory of solids" proposes that the electron energy states of atoms in a solid composition can be envisioned as bands of energy separated by gaps, rather than as discrete energy states (e.g., as seen for free atoms). Conductivity is determined by the availability of electrons in the conduction band, e.g., the lowest unoccupied molecular orbital (LUMO), which in turn is dependent upon the band gap, e.g., the energy necessary for an electron to transition between the valence band, e.g., the highest occupied molecular orbital (HOMO), and the conduction band. In conductive compositions, electrons are readily available since the valence and conduction bands overlap, while in insulators, electrons are not available due to a prohibitively large band gap. However, in semiconductor compositions, the band gap between the HOMO and LUMO is not insurmountable given a moderate input of energy (such as that provided by photon absorbance).

Selecting a Ligand Composition

Association of a ligand composition with the surface of a nanostructure can be used to alter, or modulate, the HOMO and/or LUMO energy levels of the resulting ligand:nanostructure composition, potentially altering the band gap. In addition, the presence of a charge distribution from a dipole within the ligand composition can be used to either assist in the transport of electrons and/or holes.

In some embodiments, the method of the invention is performed using a ligand composition having an energy level that is aligned with the energy level of the nanostructure.

In an alternate embodiment of the methods, modulating the energy level of the nanostructure comprises decreasing the HOMO level of the valence band. This can be achieved using a ligand composition having a dipole that comprises an electron withdrawing moiety. Exemplary dipoles having electron withdrawing characteristics include, but are not limited to, the boron-containing ligands described previously (e.g., carboranes, boron-functionalized polyhedral oligomeric silsesquioxanes, and [aryl-boron]$_n$ oligomers). Butyl boronic acid and 4-trimethylsilylphenyl boronic acid can also be used as dipole compositions in the methods of the invention. Dipole ligands with electron-withdrawing characteristics also include light-activated intramolecular salts such as spiropyrans, as well as fluorine-containing compositions, such as trifluoroacetic acid, SiF, and SiF derivatives, as well as ammonium carboxylate-modified phosphonic acids.

In a further embodiment of the methods, modulating the energy level of the nanostructure comprises increasing HOMO level of the nanostructure. This can be achieved, for example, by employing a ligand composition having a dipole comprising an electron donating moiety. Exemplary dipoles having electron donating characteristics include, but are not limited to, conjugated aromatic phosphonic acid ligands such as those provided in PCT Publication No. WO2004/022714, supra.

Associating the Ligand Composition with the Nanostructure

The ligand compositions are coupled to or otherwise associated with to the surface of the nanostructure via the nanostructure binding moiety, or "head group". Association of the nanostructure binding moiety portion of the dipole ligand composition with the surface of a nanostructure can be achieved by any of a number of approaches known in the art.

Often the nanostructures employed in the methods and compositions of the invention have one or more surfactants ("growth ligands") associated with the nanostructure surface (e.g., for solubilizing the nanostructure during the synthesis procedure). Typical surfactants employed in nanostructure synthesis include trioctyl phosphine (TOP), trioctyl phosphine oxide (TOPO), hexadecyl phosphonic acid (HDPA), octadecyl phosphonic acid (ODPA), and tri-n-butyl phosphine (TBP), as well as various long chain carboxylic acids (e.g., fatty acids, such as stearic, palmitic, myristic, lauric, capric, caprylic, caproic and butyric acids, as well as other saturated or nonsaturated lipid-like structures).

In some embodiments of the methods, the dipole-containing ligand is coupled to the nanostructure surface by performing a "ligand exchange" with the currently-coupled growth ligand. Since the growth ligand typically has a weaker association with the nanostructure than the dipole-containing ligand, it can be readily exchanged, e.g., by mass action. In one embodiment, exchanging the growth ligand for the ligand composition of the invention involves suspending or dissolving the nanostructures in an organic solvent, and combining the suspended nanostructures with the ligand composition. Solvents that can be used for the exchange process include any that are typically employed in conjunction with nanostructure synthesis and processing, such as toluene, chloroform, chlorobenzene, and the like. The temperature at which the exchanging step is performed will depend upon the ligands involved and may range from room temperature to elevated temperatures equal or greater than 100° C., 200° C., 300° C. and the like. For example, ligands comprising sulfonic acid moieties can be exchanged without substantial heating, and the process optionally can be performed at room temperature.

In another embodiment, the nanostructures are coupled to or associated with a substrate surface (e.g., a solid phase embodiment rather than in solution). The organic surfactants on the nanostructure surface can be removed in situ, for example, via a low temperature organic stripping process (at temperatures<500° C., and optionally between 200-350° C.). The stripping process is optionally followed by oxidation using, e.g., a reactive oxygen species. The replacement ligand (e.g., the dipole-containing ligand) is subsequently applied to the nanostructure by any of a number of techniques known in the art (vapor deposition, spraying, dipping, etc.).

Optionally, the nanostructures can be synthesized or grown in the presence of one or more dipole-containing ligand compositions.

Providing the Nanostructures

The nanostructures employed in the methods of the invention can be fabricated from essentially any convenient materials and fabricated by a number of mechanisms known to one of skill in the art. For example, the nanocrystals can comprise inorganic materials, e.g., a semiconducting material selected from a variety of Group II-VI, Group III-V, or Group IV semiconductors, and including, e.g., a material comprising a first element selected from Group II of the periodic table and a second element selected from Group VI (e.g., ZnS, ZnO, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and like materials); a material comprising a first element selected from Group III and a second element selected from Group V (e.g., GaN, GaP, GaAs, GaSb, InN, InP, InAs, InSb, and like materials); a material comprising a Group IV element (Ge, Si, and like materials); a material such as PbS, PbSe, PbTe, AlS, AlP, and AlSb; or an alloy or a mixture thereof. Metals such as Pd, Pt, Au, Ag, Ni, Fe, Zn, Sn, and Co can also be used in the synthesis of nanostructures for use in the invention. Further details regarding nanocrystalline structures for use in the present invention can be found, e.g., Scher et al. U.S. patent application Ser. No. 10/656,802, filed Sep. 4, 2003, incorporated herein by reference in its entirety for all purposes. Furthermore, nanostructure size can be controlled by any of a number of convenient methods that can be adapted to different materials. See, e.g., Scher et al. U.S. patent application Ser. No. 10/796,832, filed Mar. 10, 2004, and Scher et al. U.S. Provisional Patent Application Ser. No. 60/544,285, filed Feb. 11, 2004. See also references herein.

The type of nanostructure employed is determined in part by the purpose for which it is intended. Nanostructures for use in the methods described herein include, but are not limited to, nanocrystals, nanodots, nanowires, nanorods, nanotubes, nanoparticles, branched nanocrystals, and the like. While any of these nanostructure embodiments can be used in the invention, spherical or nearly spherical nanostructures such as nanodots and/or quantum dots are particularly useful for the generation of nanostructure-based photovoltaic devices. For many embodiments, the diameter (e.g., a first dimension) of the nanodot or quantum dot is less than about 20 nm, or 15 nm, or 10 nm, and optionally less than about 8 nm, 6 nm, 5 nm, or 4 nm. In some embodiments, the nanostructure diameter ranges from about 2 nm to about 4 nm, or optionally less than or equal to about 3.5 nm.

In one preferred embodiment, the methods of the invention employ nanostructures comprising a boron containing ligand composition such as compound 16 and a nanostructure comprising InP or CdSe.

Optionally, the nanostructures are associated with the surface of a substrate, such as a silicon wafer or a TEM grid. Exemplary compositions for functionalizing the substrate surface include a silicon nitride coating, a silane ligand having a nanostructure binding moiety, or other chemical moiety that can provide a proton for hydrogen-bonding to the coated nanostructure (e.g., amine, alcohol, phosphonate, fluorine or other non-carbon heteroatom).

Methods for Electron Sweeping

The present invention also provides methods for creating an internal bias field in a nanostructure composition, e.g., for extraction of electrons or holes. The method includes the steps of coupling a photoactivatable composition to a surface of a nanostructure, which composition forms a dipole upon activation, and activating the composition and creating the dipole, thereby forming an internal bias field.

In some embodiments, the photoactivatable composition includes an intramolecular salt, and optionally a light-activated intramolecular salt. The spiropyran ligands described herein are exemplary light-activated intramolecular salts that can be used in the methods.

Optionally, the method further includes the step of extracting one or more holes or electrons from the nanostructure, e.g., by transporting the electrons or holes toward an electrode. The internal bias fields thus created are particularly useful for nanostructure components of photovoltaic cells.

Methods for Reducing Charge Diffusion

In a further aspect, the present invention provides methods for reducing charge diffusion among a plurality of nanostructures, e.g., nanodots, and particularly quantum dots. The methods include the steps of coupling a ligand composition comprising an electron withdrawing group to a surface of a member nanodot (or quantum dot or other nanostructure), and forming a dipole on the surface of the member nanodot and increasing the electron affinity of the nanodot, thereby reducing any charge diffusion (such as lateral charge diffusion) among the nanodots. Optionally, the nanostructures thus formed are used in the compositions and methods for post-deposition shell formation as described herein.

Many of the ligand compositions of the present invention have electron withdrawing characteristics and can be utilized as electron-withdrawing compositions in the present methods (e.g., silicon oxide cage complexes such as silsesquioxanes). In some embodiments, the electron withdrawing composition includes a fluorine atom. For example, fluorine-containing ligand compositions such as $F^-$, SiF, an SiF derivative, or a fluorine polymer such as polytetrafluoroethylene can be employed in the methods. In other embodiments, the ligand composition is a boron-containing composition (e.g., an arylboron oligomer or a boronic acid composition). Optionally, the electron withdrawing composition includes a nanostructure binding group, such as a phosphonic acid moiety, phosphonate ester, or other nanostructure binding moiety such as those described herein, for coupling to the nanostructure surface.

Optionally, the first and second properties of the ligand compositions of the present invention are photochromism-related properties (e.g., involving color changes induced in the coating by an incoming stimulus, such as light or other incident electromagnetic radiation). In some embodiments, the electron withdrawing composition comprises a light-activated intramolecular salt, e.g., a spiropyran. Exemplary intramolecular salts for use in the methods and compositions of the present invention include, but are not limited to, $HOOCCH_2CH(NH(CH_3)_2)CH_2CH_2PO_3H_2$. See also Léaustic et al. "Photochromism of cationic spiropyran-doped silica gel" *New. J Chem.* 25:1297-1301 (2001) and references cited therein.

Additional ligand compositions for use in the methods include, but are not limited to, the silicon oxide cage complexes and silsesquioxane compositions described above and in U.S. Provisional Patent Application Ser. No. 60/578,236, filed Jun. 8, 2004. For example, boron- or other metal-substituted silsesquioxane compositions can be employed in the methods.

The methods for reducing charge diffusion are particularly useful when employed in the productions of compositions for use in discrete quantized photon generation and transfer media, and/or discrete quantized charge storage or charge transfer media. Thus, in one class of embodiments, the plurality of nanodots (or quantum dots or other nanostructures) comprises discrete quantized photon generation and transfer media or discrete quantized charge storage or charge transfer media.

The present invention also provides one or more (e.g., a plurality of) nanodots (for example, quantum dots) or other nanostructures having reduced charge diffusion, as prepared by the methods described herein. The nanostructures optionally have a rigid shell formed post-deposition of the ligand composition, e.g., a rigid shell comprising silicon or silicon oxide. The nanostructures can be of essentially any material, size, and/or shape. In one preferred class of embodiments, a diameter of the nanostructures is less than 6 nm, e.g., less than 3.5 nm.

Methods for Fabricating a Memory Device

The present invention also provides methods for fabricating a nanostructure-based memory device that uses the nanocrystals to store charge. As described in Coe et al. 2002, supra, core/shell CdSe/ZnS semiconductors can be deposited on/in a layer of conducting organic material. However, there are several problems with this previously described method. First, the thin ZnS shell generated by this method does not have a high enough energy barrier to prevent leakage of the charge out of the nanocrystal. While this problem could theoretically be addressed by growing a very thick ZnS shell, this approach is synthetically impractical. After deposition of several monolayers of shell, the strain causes defect formation, and/or the nanocrystals become insoluble, thereby providing a practical limitation to feasible shell thickness. Furthermore, the spacing between the thickly coated nanocrystals would be too large to meet the packing density desired for memory applications. The problem might also be addressed by growing a core (CdSe) shell (ZnS) and a third shell ($SiO_2$), an approach that is synthetically feasible but has similar issues as to those listed above. The present invention takes the novel approach of performing a ligand exchange directly onto the nanostructure (for example, small, roughly spherical CdSe or Pd nanocrystals) using a ligand composition as provided herein (e.g., a modified silsesquioxane ligand). (Alternately, as noted, the nanostructure can be grown in the presence of the ligand composition.) Preferably, the first coating of ligand can be converted or cured into an oxide, and will maintain the nanostructure solubility in organic solvents for deposition purposes.

The methods for fabricating a nanostructure-based memory device that uses the nanocrystals to store charge include the steps of a) providing a plurality of nanostructures the members of which have associated therewith a weakly binding growth ligand; b) exchanging the growth ligand with a replacement ligand and forming a first coating on the member nanostructures; c) associating the coated member nanostructures with a surface of a substrate; and d) converting the first coating to a second coating that differs in one or more electrical, optical, physical or structural properties, thereby fabricating a nanostructure-based memory device. In a related class of embodiments, steps a and b are replaced by a single step, in which the nanostructures are synthesized in the presence of the ligand, whereby the ligand forms a first coating on the member nanostructures. Preferably, nanoparticles having spherical, nearly spherical, and/or isotropic geometries (such as nanodots and/or quantum dots) are most effective for close packing of the nanostructures. Exchanging the growth ligand or surfactant for a replacement ligand of the first coating can be done, for example, by mass action exchange. To facilitate this process, the binding constants for the weakly bound growth ligand are preferably less than those of the ligand for use in the first coating.

One advantage to this approach to nanostructure synthesis is that the nanostructure product contains fewer organic contaminants than those prepared by methods currently available. Another advantage is that the length of the replacement ligand can be tuned to control the diameter of the coated nanostructure and thus properly space the nanocrystals apart to reduce and/or prevent charge leakage, while still allowing high density packing.

Devices

Many electronic and optical applications can be manufactured using the nanostructure-containing compositions of the present invention. Particularly, any device that employs (or can be devised to employ) nanodot nanostructures would benefit from the compositions and methods of the present invention. For example, various electronic applications such as transistors and memory devices could be prepared using the nanostructure-containing compositions of the present invention. Light emitting applications, such as LEDs, back plane lighting for LCDs, phosphors, PVs, photodetectors, and photodiodes could also employ the nanostructure-containing compositions of the present invention, as could other optoelectronic devices such as photovoltaic devices. Furthermore, the coated nanostructures could be employed in signal dampening compositions and/or as detectable labels (e.g., based upon a second optical property having a specified emission wavelength.)

The nanostructure-containing compositions of the present invention are particularly useful for the construction of flash memory constructs. Flash memory is a type of electrically-erasable programmable read-only memory (EEPROM) that can be rapidly erased and reprogrammed Devices utilizing this type of constantly-powered, nonvolatile memory can operate at higher effective speeds than standard EEPROM devices, since the memory is altered in blocks, instead of one byte at a time.

Flash memory typically encodes a single bit per cell, which comprises two transistors (a control gate and a floating gate) separated by a thin oxide layer. The cell is characterized by the specific threshold voltage between the two gates. Electrical charge is programmed/stored on the floating gate, which also controls the two possible voltage levels between the transistors (the on/off status of the cell). Multi-bit technology is also being developed, in which the cells have two or more voltage thresholds (i.e., the voltage across each cell has been divided into greater than two levels). Additional details of nanostructure-based memory devices, transistors, and the like can be found, e.g., in Duan et al. U.S. patent application Ser. No. 11/018,572, filed Dec. 21, 2004.

As noted herein, unregulated signal transmission between proximal signal carriers (cross-talk) reduces the performance/efficiency of a given device. One mechanism by which cross-talk among nanostructures in a nanostructure-containing device can be reduced is by increasing the distance between the nanostructures. This approach is particularly useful when dealing with nanoscale structures such as quantum dots. Increasing the distance between adjacent quantum dots can be accomplished by forming a rigid shell encompassing each member dot, thereby controlling the distance between them. The rigid shell is formed after deposition of a first coating onto the discrete nanostructures, thereby maintaining the discrete (physically separate) character of the individual nanostructures. If made out of an appropriate (e.g., dielectric or nonconductive) material, the rigid shell can also provide another mechanism for reducing cross-talk between nanostructures.

The nanostructure-containing compositions of the present invention can be prepared at densities of $10^{10}/cm^2$, $10^{11}/cm^2$, $10^{12}/cm^2$, or greater without loss of quantum confinement or increased cross-talk between member quantum dots.

The present invention provides novel processes for producing heterostructural nanocrystals, e.g., nanocrystals that are comprised of two or more different compositional elements where the different elements together impart useful properties to the nanocrystals. As noted herein, such heterostructures are typically embodied in a core-shell orientation, where a core of a first material is surrounded by a shell of a second material. It is worth noting that the first material can comprise a conductor, a semiconductor, or an insulator (e.g., a dielectric), and the second material can likewise comprise a conductor, a semiconductor, or an insulator (e.g., a dielectric), in any possible combinations (e.g., two conductive materials, a conductive material and an insulator, etc.). The methods of the present invention provide flexibility of processing to allow more facile fabrication of these nanocrystals, as well as manipulation of certain parameters, e.g., sizes in the sub-10 nm range, that were previously not attainable. As a result, it is expected that any application to which typical core-shell nanocrystals were to be put would be a potential application for the compositions of the present invention, e.g., those nanocrystal compositions made in accordance with the processes described herein. In addition, a variety of additional applications will be enabled by the abilities that are gained from these novel processes.

Methods for Reversible Modification of Nanostructures

For some applications, e.g., fabrication of certain nanostructure-based devices, nanostructures must withstand high temperature processing, e.g., without melting and fusing with adjacent nanostructures. Although nanostructures comprising a material with a high melting point can be selected for use in such applications, all materials have their melting point lowered as the physical size of a structure is reduced to the nanometer range; high temperature processing steps can thus be problematic even for high melting point materials.

The present invention provides novel processes for reversibly modifying nanostructures, e.g., nanostructure components of semiconductor devices, to protect the nanostructures from subsequent process steps. As one specific example, the methods of the invention can be used to oxidize palladium quantum dots (e.g., by a high temperature anneal in an oxidizing atmosphere), increasing their resistance to fusion during the process of encapsulating the dots in an overlying dielectric while fabricating a flash memory device. The oxidation can be reversed (e.g., by a high temperature anneal in a reducing atmosphere) to convert the palladium oxide back to pure (or substantially pure) palladium, to capitalize on the properties of palladium metal for device performance. It is worth noting that the methods of the invention can protect nanostructures of any of variety of materials, shapes, and sizes during a variety of subsequent manipulations, including but not limited to exposure to high temperatures.

One general class of embodiments thus provides methods of reversibly modifying nanostructures. In the methods, one or more nanostructures comprising a metal are provided. The metal is oxidized to produce a metal oxide, and the nanostructures are processed. The metal oxide is then reduced to provide the metal.

The metal can be oxidized by heating the nanostructures in an oxidizing atmosphere (e.g., one comprising oxygen). The nanostructures are typically heated to a temperature between about 200° C. and about 700° C. (e.g., between about 200° C. and about 500° C.). Similarly, the metal oxide can be reduced by heating the nanostructures in a reducing atmosphere, e.g., an atmosphere comprising hydrogen, e.g., a forming gas (i.e., 5% $H_2$ in $N_2$). It will be evident that the reactive gas(es) are preferably able to access the nanostructures through any material(s) surrounding the nanostructures. Alternatively, the nanostructures can be at least partially reduced by heating in a nitrogen atmosphere. The nanostructures are typically heated to a temperature between about 200° C. and about 700° C. (e.g., between about 200° C. and about 500° C.).

The nanostructures to be modified can be of essentially any size and/or shape. Thus, for example, the nanostructures can include one or more nanowires, nanorods, nanotubes, branched nanocrystals, nanotetrapods, tripods, bipods, nanocrystals, nanodots, quantum dots, nanoparticles, branched tetrapods, or a combination thereof. In one class of embodiments, the nanostructures are substantially spherical nanostructures.

The methods can be used for nanostructures comprising any metal that can undergo reversible oxidation. For example, the metal can be a noble metal (e.g., Au, Ag, or Pt) or a transition metal (e.g., Ni, Fe, Sn, or Zn). In one preferred class of embodiments, the metal is Pd; in this class of embodiments, the metal oxide is typically PdO. The entire nanostructure or a portion thereof (e.g., a surface layer) can be oxidized. For example, greater than 10% of the metal comprising a population of nanostructures can be oxidized, e.g., greater than 20%, greater than 50%, greater than 75%, or even greater than 90%. Oxidation (and, conversely, reduction) can be monitored, e.g., via a technique such as energy dispersive spectrometry (EDS).

As noted, such reversible oxidation can protect nanostructures during processing, e.g., certain device fabrication steps that are performed at high temperature. Thus, for example, in one class of embodiments, processing the nanostructures comprises exposing the nanostructures to a temperature between about 200° C. and about 750° C. (e.g., a temperature greater than about 250° C., greater than about 500° C., or greater than about 600° C.), or even to a temperature greater than about 750° C. Such elevated temperatures can be encountered, for example, when disposing a dielectric on the nanostructures.

The nanostructures can be protected, e.g., from fusion at high temperature, by reversible oxidation. Additionally (or alternatively), the nanostructures can be protected by a coating such as those described herein. Thus, in one class of embodiments, the one or more nanostructures provided have a first coating associated with a first surface of each nanostructure. The first coating has a first optical, electrical, physical or structural property, and is capable of being converted to a second coating having a different optical, electrical, physical or structural property. The first and/or second coatings can be, e.g., any of those described herein. Thus, for example, the second coating can comprise an oxide, e.g., $SiO_2$, optionally formed from a silsesquioxane composition such as those described herein. The first coating can be converted to the second coating by heating the nanostructures in an oxidizing atmosphere; it will be evident that the conversion can be simultaneous with oxidation of the metal. The coating (e.g., $SiO_2$) can help maintain physical separation between the nanostructures and thus reduce the tendency for adjacent nanostructures to fuse when exposed to high temperatures. Silsesquioxane ligands contain substoichiometric oxygen for formation of $SiO_2$; curing a first coating comprising a silsesquioxane in an oxidizing atmosphere can thus form a better quality $SiO_2$ second coating, which can also (or alternatively) assist in blocking nanostructure fusion.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Preparation of Closely Packed Nanostructure Monolayers

A method for preparing a substrate having closely packed nanostructures is depicted schematically in FIGS. 3 and 4. A nanodot (depicted as a sphere) is synthesized with surfactants that coat the surface. The surfactants are ligand-exchanged for the silsesquioxane or other silicate ligand (L).

A selected substrate (e.g., a silicon dioxide wafer) is coated with a silane ligand bearing a nanostructure binding head group (B). The silane ligands interact and associate into a self assembled monolayer of surface assembly ligand (SAL) on the substrate surface, providing a nanostructure-binding interface (as indicated by the perpendicular arrows). An exemplary surface assembly ligand includes a cyclic dimethyl amino moiety and a $SiMe_2$ group coupled together via a linker (cyclic dimethyl amino-organic spacer-$SiMe_2$).

The ligand exchanged nanodots are then put on the SAL substrate by spin coating or dip coating with the solvent containing the dots. The excess dots are washed off the substrate, resulting in a monolayer of nanodots insulated with silicon dioxide containing ligands. Due to the monolayer nature of the surface assembly ligand, the nanodots are closely packed (shown in side view in FIG. 4). The nanostructure-bound substrate is then thermally annealed to cure the layer, thus converting the first coating (for example, a phosphosilicate ligand) into a second coating (a shell of $SiO_2$). The resulting annealed surface is optionally treated to spin coating of another layer (a topcoat or overlay) of silicate and thermal curing, to produce a nanodot memory device.

Example 2

Synthesis of Heptacyclopentyl POSS Disilanol Diethoxyphosphate

Figure 6:
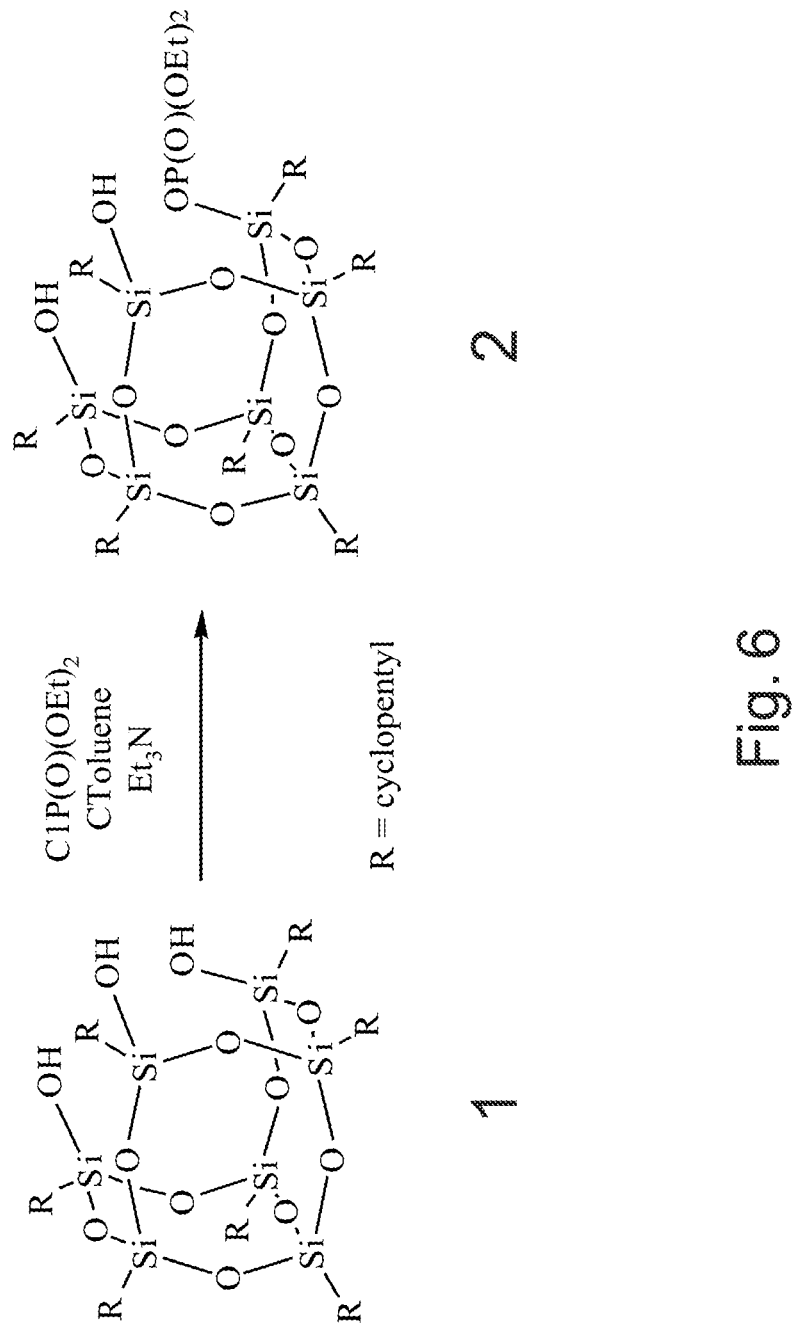
FIG. 6 provides an exemplary synthesis protocol for the production of the silsesquioxane ligand heptacyclopentyl POSS disilanol diethoxyphosphate.

Synthesis of the exemplary polyhedral oligomeric silsesquioxane (POSS) ligand heptacyclopentyl POSS disilanol diethoxyphosphate 2 was performed as provided herein (FIG. 6). All procedures were carried out under an inert atmosphere using Schlenk technique. The solvents were dried over 4 Å molecular sieves and degassed with three freeze-vacuum-thaw cycles. The heptacyclopentyl POSS trisilanol 1 was dried by static vacuum in a dessicator with phosphorous pentoxide for 12 hours, and diethyl chlorophosphonate (Cl—P(O)(OEt)$_2$ was vacuum transferred before use. Mass spectrometry was performed at Scripps Research Institute in La Jolla, and $^{31}$P {$^1$H} NMR spectroscopy was performed with a Bruker FT NMR using $^{31}$P at 162 MHz.

The reaction was set up in a 50 mL Schlenk flask. Heptacyclopentyl POSS trisilanol 1 (1.00 g, 1.14 mmol) was dissolved in a combination of toluene (10 mL) and triethylamine (15 mL) and produced a clear solution. Then ClP(O)(OEt)$_2$ (0.650 g, 0.545 mL, 3.77 mmoles) was added by syringe while stirring over 1 minute. After about 5 minutes, the clear solution turned cloudy. It was stirred overnight under argon.

Approximately 20 hours after the addition of ClP(O)(OEt)$_2$, the volatile components were removed by vacuum transfer. The residue was extracted with hexane (3×8 mL) and the volatiles removed again by vacuum transfer. The residue was dissolved in 1.25 mL of toluene and precipitated out of solution as an oil with 6 mL of acetonitrile. The upper phase was discarded and the precipitation process repeated twice. Then the oil was dissolved in 6 mL of THF, 2 mL of toluene and eventually about 6 mL of acetonitrile. The last solvent was added slowly with mixing until the solution turned cloudy. Then the mixture was cooled to −35° C. overnight, which produced some white micro-crystals. The supernatant was removed and the volatile solvents removed by vacuum transfer until at about one third of the original starting volume remained, thus providing a substantial quantity of white micro-crystals. The remaining supernatant was removed leaving the product in the flask. Then the white crystalline product 2 was dried under vacuum until a pressure of <0.010 torr was attained for 1 hour. The product was isolated as white micro-crystals 0.320 g, 0.313 mmol or 27.5% yield. Mass Spec: ESI-TOF(−) m/z 1034 [M-H+ Na], ESI-TOF(+) m/z 1011 [M-H]. NMR $^{31}$P {$^1$H} NMR (162 MHz, Tol-d$_8$, 25 C) δ −11.3 (s, 1P).

This reaction also works with 2.0 equivalents of Cl—P(O)(OEt)$_2$ and 2.0 eq Et$_3$N or pyridine in toluene. The reaction procedure was performed as described above, including the hexane washes, and the product was isolated by crystallization at −35° C. from a mixed solvent system consisting of THF, toluene and acetonitrile.

Other silsesquioxane derivatives of the present invention include:
1) Closed Silicate Cage POSS molecule mono-silanol, having an organic spacer bonded to the alcohol to give an ether (aryl or alkyl derivatives), and a carbon bond on other end of the spacer leading to the nanostructure binding head group.
2) Open Silicate Cage POSS molecule tri-silanol, having three organic spacers bonded to alcohols to give a tri-ether, and the carbon bond on the other end of the spacer linking to the nanostructure binding moiety.
3) Silicate dimer (or larger oligomer) compound prepared by condensation. Difunctional Silane and mono-heteroatom functionalized POSS, having a binding group centered at middle of the difunctional Silane spacer unit.
4) Conversion of silicate closed cage from endo to exo by selective (Si—O—Si) opening of the cage (e.g., on one side) and modification of exposed di-ol with the binding head group, for side access binding or cross-linking cage molecules.

Example 3

Generation of a Monolayer of Coated Nanostructures on a SAM

The controlled self-assembly of monolayers of nanocrystals with silsesquioxane or silicate ligands tailored for charge storage applications can be achieved by various wet-process methods, such as the deposition onto self-assembled monolayers (SAMs). This approach can be used to prepare monolayers having close packed nanostructure arrays, and preferably ordered close-packed nanostructure arrays.

A self assembled monolayer consisting of a silane ligand with a binding head for the silsesquioxane or silicate ligand is applied to a substrate surface. The nanocrystals are deposited on the SAM from solution by spin-, dip-, or spray-coating, or conventional printing technologies. The excess dots are washed off the substrate resulting in a monolayer of nanocrystals insulated with silicon dioxide containing ligands.

Example 4

Generation of an Ordered Monolayer of Coated Nanostructures by Evaporation-Driven Assembly The nanostructure-containing monolayers of the present invention can alternatively be prepared by evaporation-driven assembly. In this embodiment, specially-treated substrates functionalized or layered with chemical moieties for associating with the nanostructure are not required. CdSe nanocrystals are drop-cast onto a silicon nitride substrate. The dewetting process is controlled by the composition of the surface ligand and by wicking the surface with a solvent-absorbing cleanroom cloth. By controlling the de-wetting process of the solvent, well-ordered arrays of nanocrystals can be obtained.

Example 5

Preparation of Arrayed Nanostructures for Use in Memory Devices

The present invention describes a general approach to making a memory device based on using nanocrystals for charge storage. The method was reduced to practice using CdSe nanocrystals without a shell, which were then ligand-exchanged with a silsesquioxane ligand modified with a phosphonate ester head group to bind to the nanocrystal. These nanocrystals were then deposited on an oxide-coated substrate in monolayers.

The same general approach used, however, could be readily applied to metal nanocrystals by modifying the nanocrystal synthesis to make roughly spherical metal nanocrystals with weak binding ligands, for example Pd nanocrystals. These would then be cleaned and characterized, e.g., via NMR. The ligand would be modified by attaching a different head group to the silsesquioxane, for example a thiol or sulfonate group to better bind to the nanocrystal. The ligand would be purified, and then characterized by NMR and mass spectrometry. The ligand would be exchanged onto the nanocrystal using VT-NMR to monitor the exchange. The exchanged nanocrystals would then be cleaned to remove excess ligand. The nanocrystals will then be deposited via spin-coating or evaporation onto the prepared substrate (SAM coated, functionalized, or unfunctionalized oxide substrate).

Various aspects of the present invention can be readily varied or altered while still accomplishing the synthesis of discrete coated nanostructures. The type of nanostructures employed can be varied: CdSe, any II-VI, III-V, or group IV semiconductor, any metal (including, but not limited to, Pd, Pt, Au, Ag, Ni, Fe, Sn, Zn, and Co). A narrow size distribution can be provided either during the initial synthesis, or by subsequent size selection. Furthermore, the ligand binding group for either the weakly-bound growth ligand or the first coating (e.g., oxide-related) ligand can be varied: thiol, sulfonate, sulfinate, phosphinate, carboxylate, phosphonate, phosphonate ester, amine, phosphine, etc. Various oxide ligands can be generated (upon curing) depending upon the selection of first coating and intended use, such as $SiO_x$, $TiO_x$, $VnO_x$ or other oxides. The method of deposition can also be varied beyond those described here.

Another method for forming an oxide would be to controllably oxidize the nanocrystal surface (for example, by bubbling oxygen through a dilute solution of nanocrystals) to produce an oxide that provides an energy barrier (for example, a Co core with a cobalt oxide shell). The first coating ligands of the present invention could still be applied in solution and cured after deposition of the monolayer. The approach applied in this memory application could also be used for nanocrystals that need to be embedded in a matrix, such as tagants or phosphors.

Example 6

Preparation of a Nanostructure-Based Charge Storage Device

Nanocrystal-based capacitors can be prepared, e.g., as a demonstration of the feasibility of nanocrystal-based charge storage devices such as flash memory devices. To fabricate such an example device, a silicon wafer with a 3-6 nm thick tunnel oxide layer on it is prepared. Palladium quantum dots having a ligand composition of the invention (e.g., the POSS ligand illustrated in FIG. 5F) associated therewith are prepared by surfactant exchange or by synthesis in the presence of the ligand and suspended in an organic solvent such as toluene. The nanocrystals are then spun or dropped onto the surface of the oxide-coated wafer, wet, and dried down. Excess nanocrystals are rinsed off, leaving basically a monolayer of nanocrystals on the wafer. The wafer is baked in an atmosphere comprising oxygen at 250° C. for 10-30 minutes to cure the ligand composition and form the second coating (e.g., an $SiO_2$ shell). Another oxide layer (e.g., an $SiO_2$ layer) is deposited on the nanocrystals by chemical vapor deposition, and chrome and gold are evaporated onto the oxide layer to form an electrode. The device can then be characterized by measuring CV curves before and after applying program and erase voltages.

Example 7

Synthesis of Boronic Acid-Containing Ligands

Figure 7:
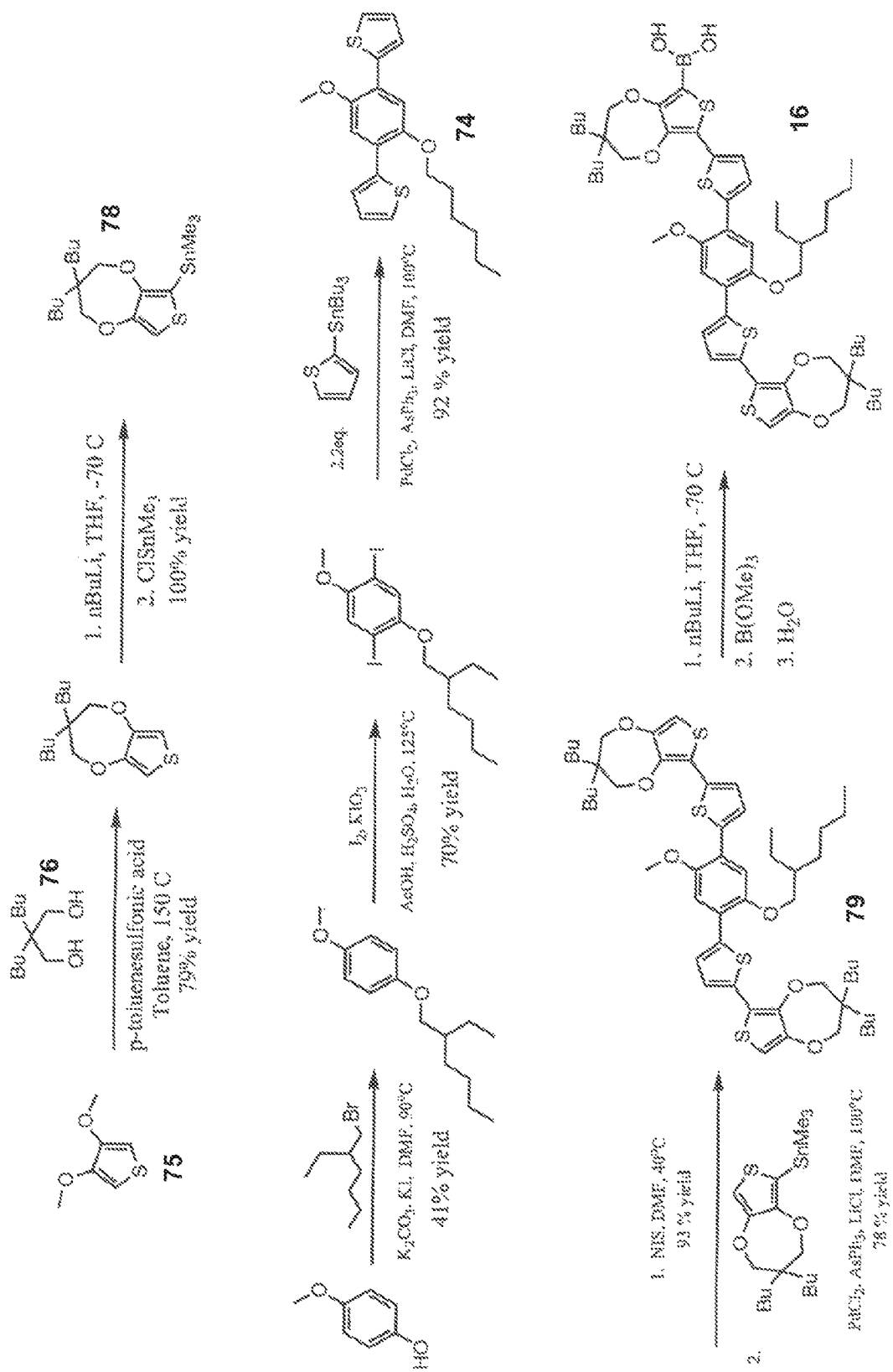
FIG. 7 depicts a chemical synthesis scheme for one embodiment of a boron-containing ligand composition of the present invention.

FIG. 7 depicts a chemical synthesis scheme for one embodiment of a boron-containing ligand composition of the present invention. The substituted thiophene tail intermediate was prepared starting with 2,3-dimethoxythiophene 75. The methoxy groups on the substituted thiophene molecule were cyclized in the presence of 2,2-dibutyl-1,3-propanediol 76, p-toluenesulfonic acid and toluene at 150° C. The cyclic substituted thiophene moiety was subjected to a stannylation reaction in the presence of trimethyltinchloride ($Me_3SnCl$) to yield a stannylated substituted thiophene 78.

Di-thiophene-containing body structure 74 was then coupled to two equivalents 78 to form intermediate body structure 79. The boronic acid moiety —$B(OH)_2$ was then added to intermediate 79 to form boron-containing ligand 16.

Figure 8:
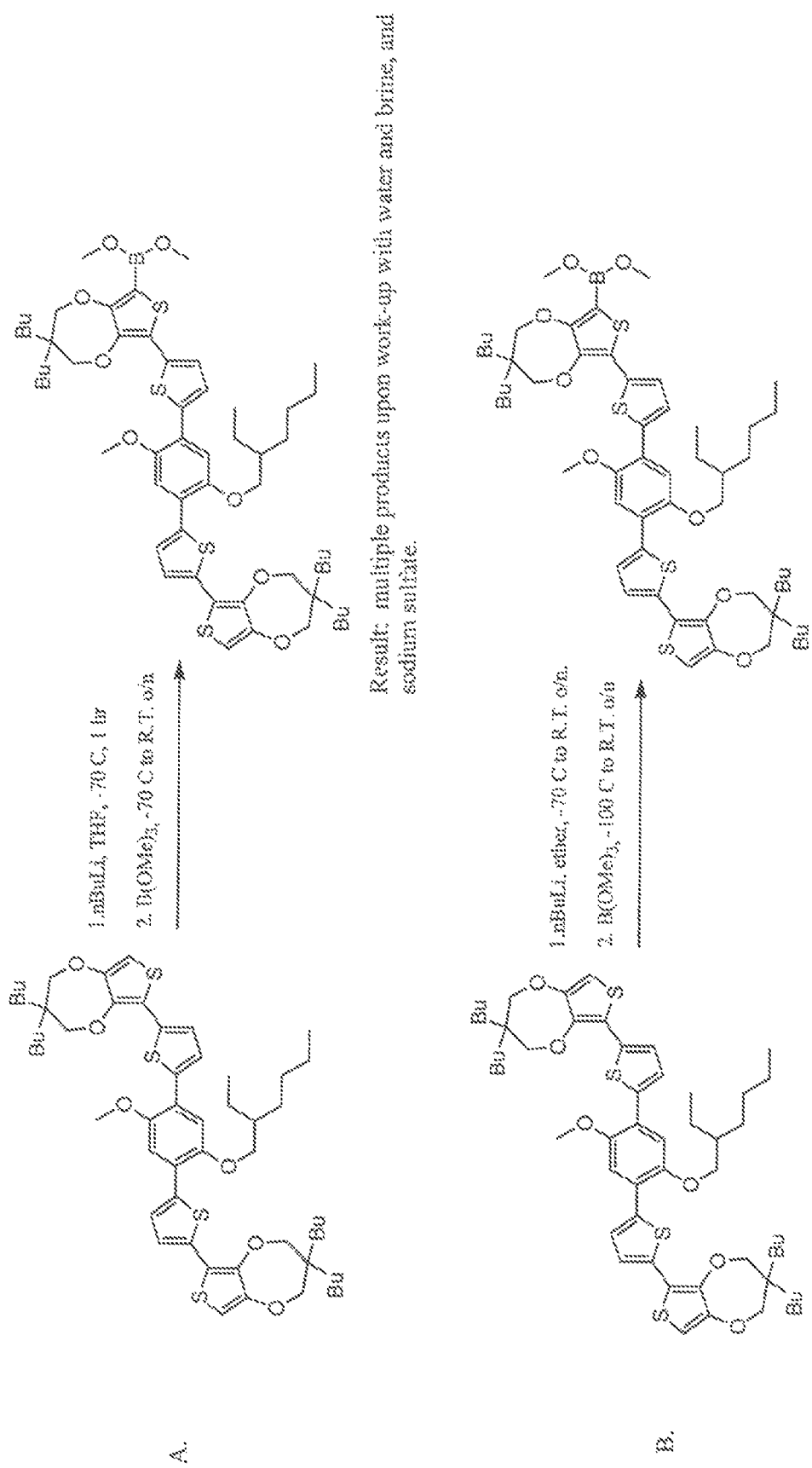
FIG. 8 depicts alternative reaction parameters optionally used in the final synthesis step of a boron-containing ligand composition.

FIG. 8 depicts two routes to the synthesis of the O-methylated form of boronic acid ligand 16.

The resulting product was analyzed by MALDI-TOF and ESI-TOF mass spectrometry (spectra not shown). A number of boron-containing derivatives are seen, such as those shown in Table 4. Intermediate 79 is also detected by MALDI-TOF MS.

TABLE 4

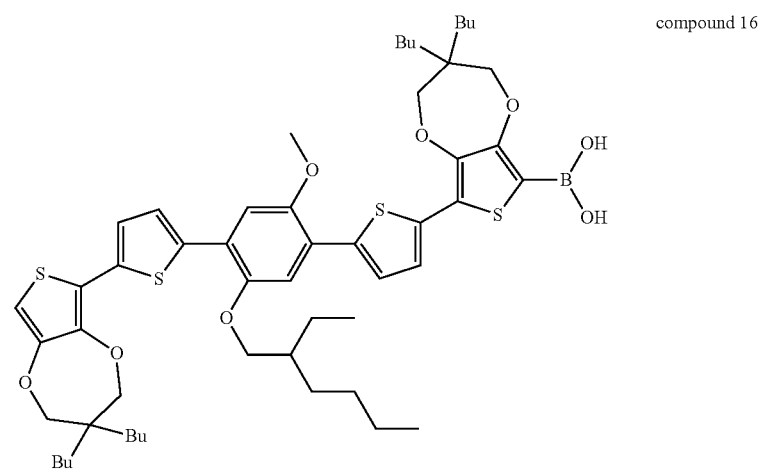

TABLE 4-continued
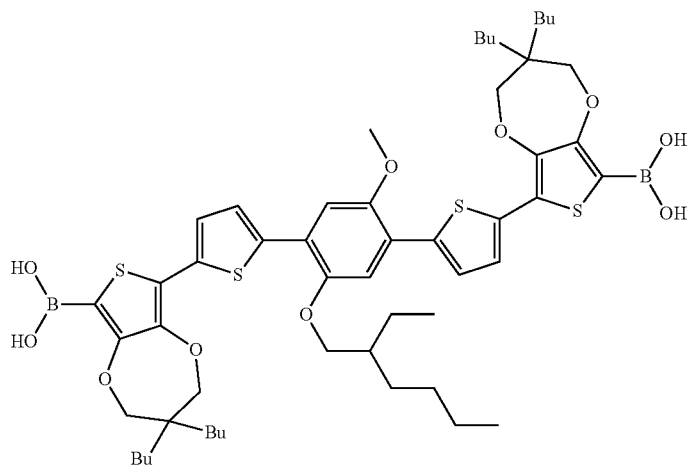
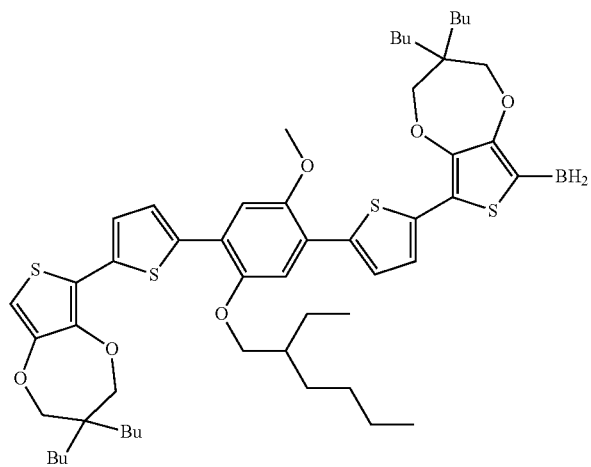
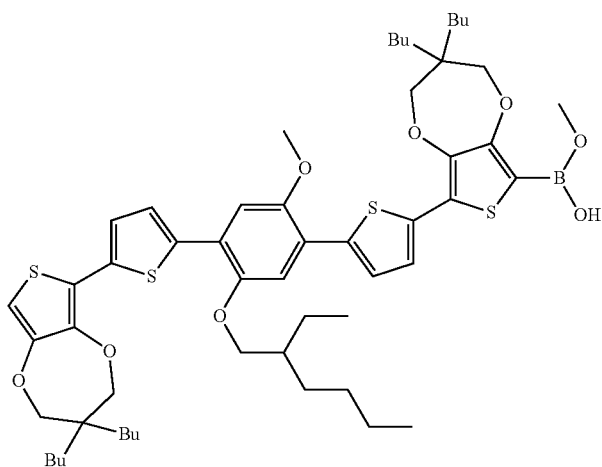

TABLE 4-continued

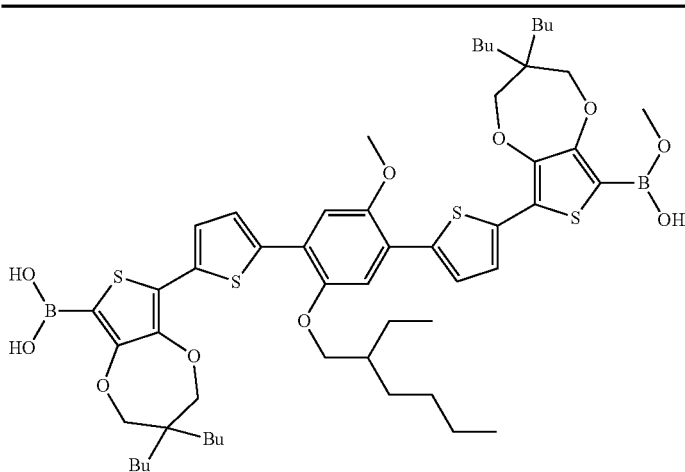

While the foregoing invention has been described in some detail for purposes of clarity and understanding, it will be clear to one skilled in the art from a reading of this disclosure that various changes in form and detail can be made without departing from the true scope of the invention. For example, all the techniques and compositions described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The invention claimed is:

1. A method for modulating an energy level of a nanostructure in the absence of a polymeric matrix, the method comprising:
providing a nanostructure having a first energy level;
selecting a ligand composition comprising a dipole, wherein the ligand composition has a second energy level as compared to the first energy level of the nanostructure; and,
associating the ligand composition with a surface of the nanostructure, thereby modulating the energy level of the nanostructure.

2. The method of claim 1, wherein the dipole comprises an electron withdrawing group, and wherein modulating the energy level of the nanostructure comprises decreasing a highest occupied molecular orbital (HOMO) level.

3. The method of claim 2, wherein the electron withdrawing group comprises one or more boron atoms.

4. The method of claim 3, wherein the ligand composition comprises butyl boronic acid, 4-trimethylsilylphenyl boronic acid, a carborane, or a boron derivative of a polyhedral oligomeric silsesquioxane (POSS).

5. The method of claim 2, wherein the electron withdrawing group comprises one or more fluorine atoms.

6. The method of claim 5, wherein the ligand composition comprises trifluoroacetic acid or a SiF derivative.

7. The method of claim 2, wherein the ligand composition comprises an ammonium carboxylate-modified phosphonic acid.

8. The method of claim 2, wherein the ligand composition comprises a spiropyran salt.

9. The method of claim 1, wherein the dipole comprises an electron donating group, and wherein modulating the energy level of the nanostructure comprises increasing a HOMO level.

10. The method of claim 9, wherein the electron donating group comprises a conjugated aromatic phosphonic acid ligand.

11. The method of claim 1, wherein the nanostructure comprises a semiconducting material.

12. The method of claim 11, wherein the semiconducting material comprises a first element selected from group II of the periodic table and a second element selected from group VI.

13. The method of claim 11, wherein the semiconducting material comprises a first element selected from group III of the periodic table and a second element selected from group V.

14. The method of claim 11, wherein the semiconducting material comprises an element selected from group IV.

15. The method of claim 1, wherein associating the ligand composition with the surface of the nanostructure comprises performing a ligand exchange.

16. The method of claim 1, wherein associating the ligand composition with the surface of the nanostructure comprises growing the nanostructure in the presence of the ligand composition.

17. A method for creating an internal bias field for extraction of electrons or holes from a nanostructure composition, the method comprising:
coupling a photoactivatable composition to a surface of a nanostructure, which composition forms a dipole upon activation; and
activating the composition and creating the dipole, thereby forming an internal bias field.

18. The method of claim 17, wherein the photoactivatable composition comprises a light-activated intramolecular salt.

19. The method of claim 18, wherein the light-activated intramolecular salt comprises a spiropyran.

20. The method of claim 17, wherein coupling the photoactivatable composition to the surface of the nanostructure comprises performing a ligand exchange.

21. The method of claim 17, wherein activating the composition comprises exposing the coupled ligand:nanostructure composition to a light source.

22. The method of claim 17, further comprising:
extracting one or more holes or electrons from the nanostructure.

23. The method of claim 22, wherein extracting the electrons or holes comprises transporting the electrons or holes toward an electrode.

24. The method of claim 17, wherein the nanostructure is a component of a photovoltaic cell.

25. A method for reducing charge diffusion among a plurality of nanostructures, the method comprising:
coupling a ligand composition comprising an electron withdrawing group to a surface of a member nanostructure; and
forming a dipole on the surface of the member nanostructure and increasing the electron affinity of the nanostructure, thereby reducing charge diffusion among the nanostructures.

26. The method of claim 25, wherein the nanostructures are quantum dots.

27. The method of claim 25, wherein the ligand composition comprises one or more fluorine atoms.

28. The method of claim 27, wherein the ligand composition comprises F—, SiF, or a SiF derivative.

29. The method of claim 27, wherein the composition comprises poly(tetrafluoroethylene).

30. The method of claim 25, wherein the composition comprises a light-activated intramolecular salt.

31. The method of claim 30, wherein the composition comprises a spiropyran.

32. The method of claim 25, wherein the composition comprises a silicon oxide cage complex.

33. The method of claim 25, wherein the composition comprises a silsesquioxane.

34. The method of claim 25, wherein the composition comprises a phosphonic acid moiety.

35. The method of claim 25, wherein the plurality of nanostructures comprises discrete quantized photon generation and transfer media.

36. The method of claim 25, wherein the plurality of nanostructures comprises discrete quantized charge storage or charge transfer media.

* * * * *